(12) United States Patent
Venkitaraman et al.

(10) Patent No.: US 8,021,851 B2
(45) Date of Patent: Sep. 20, 2011

(54) THR51 PHOSPHORYLATED HP 1β PROTEIN FOR THE ASSESSMENT OF DNA DAMAGE

(75) Inventors: Ashok Venkitaraman, Hills Road (GB); Anand Devaprasath Jeyasekharan, Hills Road (GB); Nabieh Ayoub, Hills Road (GB)

(73) Assignees: Cambridge Enterprise Limited, Cambridge (GB); Medical Research Council, London (GB)

( * ) Notice: Subject to any disclaimer, the term of this patent is extended or adjusted under 35 U.S.C. 154(b) by 60 days.

(21) Appl. No.: 12/418,038

(22) Filed: Apr. 3, 2009

(65) Prior Publication Data

US 2009/0253144 A1 Oct. 8, 2009

(51) Int. Cl.
*G01N 33/53* (2006.01)

(52) U.S. Cl. ...................................................... 435/7.1
(58) Field of Classification Search .................... None
See application file for complete search history.

(56) References Cited

OTHER PUBLICATIONS

Tockman et al (Cancer Res., 1992, 52:2711s-2718s).*
Nielsen et al (Nature, 2002, 416: 103-107).*

* cited by examiner

*Primary Examiner* — Laura B Goddard
(74) *Attorney, Agent, or Firm* — Bozicevic, Field & Francis LLP; Pamela J. Sherwood

(57) ABSTRACT

This invention relates to the finding that HP1β is phosphorylated at Thr51 at an early stage in the DNA damage response in cells. Thr51P HP1β is therefore a biomarker for DNA damage which may be useful, for example, in assessing DNA damage, cancer susceptibility or the responsiveness of an individual to DNA damaging therapies.

5 Claims, 13 Drawing Sheets

THR51 PHOSPHORYLATED HP 1β PROTEIN FOR THE ASSESSMENT OF DNA DAMAGE

This invention relates to the assessment of DNA damage in cells. This may be useful, for example, in medical research, diagnosis and therapy.

Minutes after DNA damage in a cell, the variant histone H2AX is phosphorylated by protein kinases of the phosphoinositide kinase (PIK) family, including ATM, ATR or DNA-PK 1. Phosphorylated (or γ)H2AX, which recruits molecules that sense or signal the presence of DNA breaks, activating the response that leads to repair[2,3] is the earliest known marker of chromosomal DNA breakage.

The present inventors have identified a dynamic change in chromatin that promotes H2AX phosphorylation. DNA damage is found to swiftly mobilize HP1β, which is a chromatin factor bound to histone H3 methylated on lysine 9 (H3K9me), by phosphorylation of HP1β at Thr51. Thr51P HP1β is therefore a biomarker for DNA damage which may be useful, for example in assessing cancer susceptibility or the responsiveness of an individual to DNA damaging therapies.

One aspect of the invention provides a method of assessing DNA damage in a cell comprising:

determining the level or amount of Thr51 phosphorylated HP1β protein in the cell.

The amount of HP1β protein in the cell which is phosphorylated at Thr51 (herein termed Thr51P HP1β protein) is therefore indicative of DNA damage in the cell.

The amount of Thr51P HP1β protein in the cell may be compared to the amount of Thr51P HP1β protein in control cells. An increased amount of Thr51P HP1β protein in the test cell relative to the control cells is indicative of DNA damage in the cell.

Suitable control cells may include cells in which the DNA damage response is not activated i.e. cells without DNA damage. The control cells may be of the same type as the test cell i.e. from the same tissue or lineage. In some embodiments, the amount of Thr51P HP1β protein in the control cells may be pre-determined and the value from the cell(s) tested for DNA damage compared to such pre-determined (e.g. historical or archived) control values. The provision of suitable controls will be routine for those skilled in the art.

In some embodiments, an amount of Thr51P HP1β protein above a threshold value in a cell is indicative of DNA damage in the cell.

A suitable threshold value may be determined from the amount of Thr51P HP1β protein in one or more control cells. For example, the threshold value may be calculated from the mean level of the Thr51P HP1β protein in a population of control cells. A suitable threshold value may represent a statistically significant variation from the amount of Thr51P HP1β protein in the control cells (e.g. greater than one standard deviation away from the mean level of amount of Thr51P HP1β protein in the control cells). Threshold values may be recorded or stored for subsequent use in the methods described herein.

The threshold values for the amount of Thr51P HP1β protein in a cell which is indicative of DNA damage may depend on the measurement method and instrumentation employed. Suitable threshold values may readily be determined using routine experimentation for any particular experimental set-up.

In some embodiments, the amount of Thr51P HP1β protein in the cell may be determined relative to the amount of HP1β protein in the cell which is not phosphorylated at Thr51 (Thr51 HP1β protein) i.e. HP1β protein which is either unphosphorylated or phosphorylated at positions other than Thr51. For example, the ratio of Thr51P HP1β to Thr51 HP1β may be determined.

The proportion of the total HP1β protein in the cell which is phosphorylated at Thr51 may be indicative of DNA damage in the cell.

In some embodiments, proportion of the total HP1β protein in the cell which is phosphorylated at Thr51 may be compared to the proportion in control cells. An increase in proportion of the total HP1β protein which is phosphorylated at Thr51 in the test cell relative to the control cells may be indicative of DNA damage in the cell.

A suitable cell expresses HP1β protein and may be a eukaryotic cell, for example a higher eukaryotic cell, such as a *Drosophila* or mammalian cell. In some preferred embodiments, the cell is a human cell, for example a cancer cell from a tumour sample or a tumour-derived cell line or a cell suspected of being a cancer cell.

In some embodiments, the cell may be a cultured cell obtained from a cultured cell line or tissue culture.

In other embodiments, the cell may be comprised in or isolated from a sample, such as a biopsy sample, obtained from an individual, for example, a healthy individual, an individual undergoing DNA damaging therapy (e.g. for a cancer condition), an individual suspected of having an increased risk of tumorigenesis or an individual suspected of having a cancer condition.

HP1β is widely conserved in eukaryotes and the HP1β protein may be any eukaryotic HP1β which is expressed by the cell being assessed for DNA damage. For example, the HP1β protein may be a human HP1β protein having the amino acid sequence of SEQ ID NO: 1 or may be a variant thereof, for example an allelic variant, or a homologue from a different species. HP1β may be identified in any test eukaryotic cell by reference to publicly available sequences and conventional sequence analysis tools.

The amino acid sequence of human HP1β (GeneID 10951), for example, is available on the Genbank database under accession number NP_006798.1 GI: 5803076 and is shown in SEQ ID NO:1. The nucleotide sequence of human HP1β is available on the Genbank database under accession number NM_006807.3 GI: 34147635.

A variant of the human HP1β protein may comprise a sequence having at least 60%, at least 70%, at least 80%, at least 85%, at least 90%, at least 95% or at least 98% sequence identity with SEQ ID NO: 1.

Amino acid identity is generally defined with reference to the algorithm GAP (GCG Wisconsin Package™, Accelrys, San Diego Calif.). GAP uses the Needleman & Wunsch algorithm (J. Mol. Biol. (48): 444-453 (1970)) to align two complete sequences that maximizes the number of matches and minimizes the number of gaps. Generally, the default parameters are used, with a gap creation penalty=12 and gap extension penalty=4. Use of GAP may be preferred but other algorithms may be used, e.g. BLAST or TBLASTN (which use the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), generally employing default parameters.

A variant may differ from SEQ ID NO: 1 by insertion, addition, substitution or deletion of 1 amino acid, 2, 3, 4, 5-10, 10-20 20-30 or 30-50 amino acids.

Preferably, the cell is a human cell which expresses human HP1β. Thr51 is highlighted in the human HP1β sequence of SEQ ID NO: 1. The corresponding residue in other HP1β protein sequences, for example from other species, may be readily determined using standard sequence alignment and analysis tools.

In some embodiments, the presence or amount of Thr51P HP1β protein may be determined in vivo in non-human animals, such as *Drosophila*, rodents or other laboratory animals, which are engineered to express fluorescent or luminescent reporters in the cells of interest. Suitable approaches are known in the art (see for example Lin et al *J Am Chem Soc* 2004 May 19; 126(19):5982-3)

Alternatively, the presence or amount of Thr51P HP1β protein may be determined in vitro. Any convenient technique may be employed.

Preferably, the presence or amount of Thr51P HP1β protein in cell is determined using immunological techniques, for example using an antibody molecule that binds specifically to Thr51P HP1β protein. A method of assessing DNA damage in a cell may comprise;

determining the binding of HP1β protein in the cell to an antibody which specifically binds to Thr51P HP1β protein.

The presence or amount of binding of the antibody to HP1β in the cell is indicative of the presence of DNA damage in the cell.

The cell may be treated, for example by disruption or fractionation, to allow the antibody to contact intracellular factors, in particular nuclear proteins, such as HP1β. For example, cells may be lysed using non-ionic detergents and subjected to sub-cellular fractionation or western blotting.

The cell may be comprised within a sample, for example a sample obtained from an individual. The cell may be contacted with the antibody and the binding of the antibody to Thr51P HP1β protein determined.

An antibody which specifically binds to Thr51P HP1β protein is reactive with a unique epitope formed by phosphorylation of HP1β at position 51. Preferably, the antibody specifically binds to Thr51P HP1β protein and displays no binding or substantially no binding to HP1β protein which is not phosphorylated at Thr 51(Thr51 HP1β). Furthermore, the antibody may display no binding or substantially no binding to other molecules, in particular proteins, lipids and carbohydrates, found in the mammalian cell. In some cases, the target epitope may be carried by antigens other than Thr51P HP1β protein, in which case the antibody will also be able to bind to the various antigens carrying the epitope.

An antibody for use in the present methods may bind to an epitope comprising 5 or more, 6 or more, 7 or more or 8 or more contiguous residues of SEQ ID NO: 1 which include phosphorylated Thr51. The antibody may display little or no binding to the same epitope, when Thr51 is not phosphorylated.

Suitable antibodies for use in the present methods may be obtained from immunised animals using any of a variety of techniques known in the art, and screened, preferably using binding of antibody to antigen of interest. For instance, Western blotting techniques or immunoprecipitation may be used (Armitage et al. (1992) Nature 357: 80-82). Isolation of antibodies and/or antibody-producing cells from an animal may be accompanied by a step of sacrificing the animal.

As an alternative or supplement to immunizing a mammal with a peptide, an antibody specific for Thr51P HP1β protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

The library may be screened with an HP1β epitope comprising phosphorylated Thr51 and immunoglobulin binding domains which bind to the epitope identified and isolated in accordance with standard phage display techniques.

Antibodies may be modified in a number of ways. Indeed, the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Binding of antibody molecules to Thr51P HP1β protein in a cell may be determined by any appropriate means. Tagging with individual reporter molecules is one possibility. The reporter molecules may directly or indirectly generate detectable, and preferably measurable, signals. The linkage of reporter molecules may be direct or indirect, covalent, e.g. via a peptide bond, or non-covalent. Linkage via a peptide bond may be as a result of recombinant expression of a gene fusion, encoding antibody and reporter molecule.

For example, the antibody may be labelled with a fluorophore such as FITC or rhodamine, a radioisotope, or a non-isotopic-labelling reagent such as biotin or digoxigenin; antibodies containing biotin may be detected using "detection reagents" such as avidin conjugated to any desirable label such as a fluorochrome. In some embodiments, an additional (i.e. a second) antibody may be used to detect the binding of the first antibody.

The mode of determining binding is not a feature of the present invention and those skilled in the art are able to choose a suitable mode according to their preference and general knowledge.

Suitable approaches include immunoprecipitation-western, isoelectric focussing (IEF), immunoprecipitation-IEF and immunoprecipitation-mass spectrometry, immunohistochemical staining, immunocytochemical staining, Western Blotting, immunofluorescence, enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. In some preferred embodiments, immunohistochemistical or immunocytochemical techniques may be employed. Assays may be carried out in various formats including, e.g., in automated high content microscopy formats or microtiter plate formats, using automated immunoassay analyzers known in the art. All of these approaches are well known in the art.

An antibody for use in a method described herein may be immobilised or non-immobilised i.e. free in solution.

An antibody may be immobilised, for example, by attachment to an insoluble support. The support may be in particulate or solid form and may include a plate, a test tube, beads, a ball, a filter or a membrane. An antibody may, for example, be fixed to an insoluble support that is suitable for use in affinity chromatography. Methods for fixing antibodies to insoluble supports are known to those skilled in the art. An immobilised antibody may be preferred, for example, for binding to antigens such as Thr51P HP1β protein, in solution.

The binding of the antibody to a Thr51P HP1β protein may be detected using a second antibody. The second antibody may bind to the first antibody, or may bind to a different region of HP1β, for example in a sandwich assay. Depending on the assay format employed, the second antibody may be immobilised or labelled with a detectable label.

In some embodiments, a labelled third antibody may be used to detect the binding of the second antibody.

Oncogenic stress is known to be initially checked by the DNA damage response mechanism, and overcoming this barrier is one of the early events in carcinogenesis (Halazonetis et al; Science 2008 Mar. 7; 319(5868):1352-5; PMID: 18323444; Venkitaraman; Nature 2005 Apr. 14; 434(7035): 829-30; PMID: 15829943).

Another aspect of the invention provides a method of determining the susceptibility of a tissue to tumorigenesis comprising;

determining the level or amount of Thr51P HP1β protein in one or more cells obtained from the tissue.

The amount of Thr51P HP1β in the one or more cells may be compared to the amount of Thr51P HP1β in control cells. An increase in the amount of Thr51P HP1β in the one or more cells relative to the control cells is indicative that the tissue has increased susceptibility or risk of tumorigenesis relative to normal tissue.

Suitable control cells may include cells from normal, non-cancerous tissue. The normal cells may be of the same type as the test cell i.e. from the same tissue or lineage.

In some embodiments, an amount of Thr51P HP1β protein in the one or more cells from the test tissue which is above a threshold value may be indicative that the tissue has increased susceptibility or risk of tumorigenesis relative to normal tissue.

Suitable threshold values may be determined by determining the correlation of Thr51P HP1β levels with known markers of increased cell proliferation, such as ki-67, AgNOR, BrDU incorporation or MCM staining or pathological indices that include mitotic bodies, metaplasia and dysplasia. For example, threshold levels for assessing susceptibility to tumorigenesis may be calculated using a receiver operated characteristic (ROC) analysis (see, for example Devaprasath and Chacko Neurol India 2003 September; 51(3):336-40; PMID 14652433). Threshold values may be recorded or stored for subsequent use in assessing susceptibility to tumorigenesis as described herein.

An individual having a tissue susceptible to tumorigenesis may have an increased risk of the onset of a cancer condition in the tissue, relative to the population as a whole. For example, the individual may have an increased risk of lung cancer, gastrointestinal cancer, bowel cancer, colon cancer, breast carcinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma, lymphoma or leukaemia.

The one or more cells may be obtained from tissue within an individual, for example using any conventional sampling technique. For example, the cells may be comprised in a tissue biopsy.

In some embodiments, the individual may not be suffering from or suspected of suffering from a cancer condition. The one or more one or more cells may be non-cancer cells from the individual. Methods described herein may be useful, for example, in determining whether the individual has a genetic susceptibility to endogenous DNA damage (e.g. via a germline ATM mutation) and therefore an increased susceptibility to tumorigenesis or carcinogenesis. Conveniently, the one or more one or more cells may be easily accessible cell types, such as blood leukocytes. Thr51P HP1β levels may be compared, for example by antibody staining, before and after DNA damage, and the activation of the DNA damage response determined. Thr51P HP1β is an early stage biomarker of this response and defects in this response correlate with increased susceptibility to tumorigenesis and carcinogenesis. For example, little or no increase in Thr51P HP1β levels after DNA damage relative to before, may be indicative of increased susceptibility to tumorigenesis.

In other embodiments, the individual may be suspected of or at risk of suffering from tumorigenesis. The one or more cells from the individual may be cancer cells or cells suspected of being cancer cells. Thr51P HP1β is a biomarker for DNA damage so an increased amount of Thr51P HP1β in cells from a test tissue relative to normal tissue may be indicative that the tumorigenesis or carcinogenesis has occurred in the test tissue and the individual is suffering from a cancer condition.

The presence or amount of Thr51P HP1β may be determined in the one or more cells as described above. For example, a method of determining the susceptibility of a tissue to tumorigenesis may comprise;

contacting a sample obtained from the tissue with an antibody molecule which specifically binds to Thr51P HP1β; and, determining binding of said antibody to the sample.

Increased binding of the antibody to the sample relative to control samples from the same tissue is indicative of activation of the DNA damage response in cells within the sample. Activation of this response is indicative that the tissue has an increased susceptibility or risk of tumorigenesis relative to tissue with undamaged DNA.

The binding of the antibody to samples from different regions of the tissue may be compared. Increased binding in one or more regions relative to other regions may be indicative that the one or more regions are susceptible to tumorigenesis.

The binding of said antibody to the sample may be compared with one or more control samples obtained from the same tissue, for example from an individual or population of individuals not having or susceptible to tumorigenesis. An increase in binding relative to the one or more controls is indicative that the test tissue is susceptible to tumorigenesis.

In some embodiments, binding of the antibody to the sample may be determined relative to the binding of a second antibody to the same sample. For example, the second antibody may specifically bind to HP1β which is not phosphorylated at Thr51 or a different target protein, such as a different DNA-damage associated post-translational modification, such as gamma-H2AX or phoshpho-ATM/Chk1. The amount of binding to the sample of the first antibody relative to the binding to the sample of the second antibody may be indicative that the tissue is susceptible to tumorigenesis.

For example, the susceptibility to tumorigenesis may thus be assessed by determining the ratio of HP1β which is phosphorylated at Thr51 to HP1β which is not phosphorylated at Thr51.

For example, the proportion of total HP1β in the cells which is phosphorylated at Thr51 may be determined.

The proportion of total HP1β in the cells which is phosphorylated at Thr51 may be compared to the proportion in control cells. An increase in proportion of total HP1β in the cells which is phosphorylated at Thr51 in the test cells relative to the control cells may be indicative that the test cells are from a tissue with increased susceptibility to tumorigenesis, relative to normal tissue.

The amount of Thr51P HP1β in the cells relative to the amount of one or more other DNA-damage associated post-translational modifications, may allow therapeutically useful classification of different types of response to oncogenic stress or chemotherapeutic agents.

Other aspects of the invention relate to the analysis of Thr51P HP1β to determine the efficacy or responsiveness of an individual to a DNA damaging therapy, for example in the treatment of a cancer condition, such as a condition described above.

A method of assessing the efficacy of a DNA damaging therapy for an individual or the responsiveness of an individual to a DNA damaging therapy may comprise:

measuring the level or amount of Thr51P HP1β in one or more cells obtained from an individual subjected to a regimen of treatment with the DNA damaging therapy.

The presence or amount of Thr51P HP1β may be determined as described above. For example, a method may comprise;

contacting a tissue sample obtained from the individual undergoing a regimen of DNA damaging therapy with an antibody which specifically binds to Thr51P HP1β; and, determining binding of said antibody to said sample.

The binding of the antibody is indicative of the presence or amount of Thr51P HP1β in the cell.

The DNA damaging therapy may be a cancer therapy.

The level or amount of Thr51P HP1β may be determined in one or more cancer cells, cells suspected of being cancer cells or cells obtained from cancerous tissue of the individual.

In some embodiments, the level or amount of Thr51P HP1β may be determined in one or more normal non-cancer cells from the individual, for example accessible cells such as blood leukocytes.

The level or amount of Thr51P HP1β in cancer cells (i.e. cells from tumour tissue) relative to normal cells (i.e. cells from normal tissue) may be determined. The ratio of the change in Thr51P HP1β levels in tumour tissue relative to normal tissue may be indicative of the efficacy of the regimen.

A control tissue sample may be obtained before the DNA damaging cancer therapy regimen is initiated. An increase in the amount of Thr51P HP1β after initiation of the damaging cancer therapy regimen is indicative that the regimen induces DNA damage in one or more cells of the individual and is therefore efficacious for the treatment of the individual.

The absence of any increase in the amount of Thr51P HP1β after initiation of the damaging cancer therapy regimen may be indicative that the regimen is not efficacious for the treatment of the individual; or may be indicative that the individual is defective in DNA damage repair, and therefore has increased genetic susceptibility to cancer.

The level or amount of Thr51P HP1β may be measured in samples obtained at one or more, two or more, or three or more time points during or after the treatment. The amount of change in the level or amount of Thr51P HP1β may be indicative of the level of responsiveness of the individual to the regimen.

The DNA damaging therapy may be a cancer therapy. The level or amount of Thr51P HP1β may be determined in one or more cancer cells, cells suspected of being cancer cells or cells obtained from cancerous tissue of the individual.

Alternatively or additionally, the level or amount of Thr51P HP1β may be determined in one or more normal non-cancer cells from the individual, for example accessible cells such as blood leukocytes.

The amount of Thr51P HP1β in cancer cells (i.e. cells from tumour tissue) relative to normal cells (i.e. cells from normal tissue) may be determined, before, during and/or after said regimen.

The change in the amount of Thr51P HP1β in cancer cells (i.e. cells from tumour tissue) relative to normal cells (i.e. cells from normal tissue) may be determined during treatment with the regimen. For example, the ratio of the change in Thr51P HP1β levels in tumour tissue relative to normal tissue may be determined. This may be indicative of the level of responsiveness of the individual to the regimen.

A DNA damaging therapy is a therapeutic intervention which induces DNA double strand breaks or other lesions in cellular DNA. Suitable DNA damaging therapies include irradiation and DNA damaging chemotherapeutic agents.

A DNA damaging chemotherapeutic agent is preferably a compound which induces DNA DSBs in cellular DNA. Many suitable compounds are known in the art, in particular for use in the treatment of cancer. DNA damaging chemotherapeutic agents include, for example, bleomycin and inhibitors of topoisomerase I and II activity, such as doxorubicin, etoposide and members of the tecan family e.g. irinotecan, topotecan, rubitecan.

DNA damaging chemotherapeutic agents also include compounds that indirectly induce DSBs through the disruption of DNA synthesis, for example, gemcitabine, or through the alkylation of DNA, for example, temozolomide and DTIC (dacarbazine), or through the introduction of a bulky adduct, for example platinum agents like cisplatin, oxaliplatin and carboplatin, may also be used. Other suitable chemotherapeutic agents indirectly induce DSBs through the inhibition of DNA damage repair, including for example poly(ADP-ribose) polymerase (PARP) inhibitors, such as Patrin™ (AstraZeneca). Other suitable chemotherapeutic agents include yondelis. Derivatives or salts or combinations any of these compounds may also be used.

Suitable combinations of compounds that may be used as DNA damaging chemotherapeutic agents in accordance with the invention are shown in Table 1.

Suitable dosages and regimens for DNA damaging chemotherapeutic agents are well known to medical practitioners.

DNA damaging irradiation therapy is well-known in the art, in particular for use in the treatment of cancer and any suitable technique may be used.

DNA damaging irradiation therapy includes external beam therapy, such as X-rays, gamma rays and electrons. Suitable regimes include fractionated palliative and curative regimes involving accelerated- and hyper-fractionation as appropriate and all geometric forms, conventional, 3D, 3D conformal, IMRT (intensity modulated radiotherapy), 4D and adaptive radiotherapy. (Bucci M K et al [2005] CA Cancer J Clin 55; 117-134, Haustermans et al (2004) Rays 29(3):231-6).

DNA damaging irradiation therapy also includes local/targeted therapies, such as radio active seeds or wires surgically implanted as part of a brachytherapy regime (Dale at al [1998] B J Radiol 71; 465-483); radioimmunotherapy, where a radioactive emitter is linked to an immunologic molecule such as a monoclonal antibody e.g. ibritumomab (Zevalin) (Blum K A, Bartlett N L [2004] Expert Opin Biol Ther. 4(8):1323-31); and non-immunological targeting such as radioactive microspheres delivered by injection e.g. SIR-Spheres® (Ho S et al (2001) Journal of Nuclear Medicine 42(10):1587-1589). Non-immunological targeting may also be accomplished with targeted peptide receptor therapy. For example, radiolabelled somatostatin analogues ($^{111}$In-Octreotide, $^{90}$Y-OctreoTher™, $^{177}$Lu-Octreotate) or other peptide ligands, such as Bombesin and NPY($y_1$)analogues (Krenning et al [2004] Ann NY Acad Sci. 1014(2): 234-245).

A treatment regimen is a predetermined scheme or program which defines the parameters of the treatment to which the individual is to be subjected. For example, the regimen may set out the dosage, the mode of administration and the timetable or schedule of administration of the DNA damaging agent with which the individual is to be treated.

An appropriate regimen of treatment with a DNA damaging agent can vary from patient to patient. Determining the appropriate dosage, mode and schedule of administration will generally involve the balancing of the level of therapeutic benefit against any risk or deleterious side effects of the treatments. For example, the initial dosage level and schedule will depend on a variety of factors including, but not limited to, the activity of the particular DNA damaging agent, the chosen route of administration, the time of administration, the rate of excretion of the compound, the duration of the treatment, other drugs, compounds, and/or materials used in combination, and the age, sex, weight, condition, general health, and prior medical history of the individual. The parameters of the regimen may be optimised for an individual using the methods described below.

The initial treatment regimen will ultimately be at the discretion of the physician, although generally the dosage and other parameters will be selected in order to achieve DNA damage as assessed using the methods described herein, without causing substantial harmful or deleterious side-effects.

In the absence of any change in the level or amount of Thr51P HP1, the regimen may be altered, for example by increasing the dosage, frequency of administration and/or duration of treatment, and the responsiveness of the individual to the altered regimen determined. This may be repeated until a change in the level or amount of Thr51P HP1β protein is observed. A treatment regimen which changes the level or amount of Thr51P HP1β protein may be identified.

In some embodiments, a treatment regimen which produces a change in the level or amount of the Thr51P HP1β protein may be altered, for example, by increasing the dosage, frequency of administration and/or duration of treatment, and the responsiveness of the individual to the altered regimen determined. This may be repeated until no further change in the level or amount of Thr51P HP1β protein is observed. A treatment regimen which produces a maximal change in the level or amount of Thr51P HP1β protein with acceptable toxicity levels may be identified.

In some embodiments, following identification of a treatment regimen which changes the level or amount of the Thr51P HP1β or produces a maximal change in the level or amount of Thr51P HP1, the safety, tolerability and/or pharmacokinetic effects of the regimen may be assessed in one or more individuals.

The progress of a DNA damaging therapy regimen may be monitored in an individual using the methods described herein, for example to ensure that the pharmacological effect is sustained in the individual throughout the duration of the treatment. A method for monitoring the treatment of a cancer condition in individual with a DNA damaging therapy may comprise:
  (a) subjecting the individual to a regimen of DNA damaging therapy; and
  (b) monitoring in one or more cells of the individual the level or amount of Thr51P HP1β protein during said treatment.

The level or amount of Thr51P HP1β protein may be monitored by periodically obtaining samples from the individual and measuring the level or amount of Thr51P HP1β protein in the samples obtained.

A change in the level or amount of the Thr51P HP1β protein or the ratio of Thr51P HP1β protein in tumour relative to normal tissue in response to the regimen is indicative that the regimen is effective for therapy in the individual. The change may be sustained over the duration of the regimen, for example, because Thr51P HP1β protein levels remain above or below a predetermined value or within a predetermined range of values throughout the treatment, A regimen which is found to be not fully effective may be altered, for example by altering the dosage or schedule, to restore the change in the level or amount of Thr51P HP1β; for example, by restoring Thr51P HP1β levels to above or below a predetermined value or within a predetermined range of values. In some embodiments, the dosage, intensity or frequency of administration of the DNA damaging therapy may be increased if the level or amount of Thr51P HP1β or the ratio of Thr51P HP1β protein in tumour relative to normal tissue falls below a predetermined value.

The predetermined values for the level or amount of the Thr51P HP1β in the sample or the ratio of Thr51P HP1β protein in tumour tissue relative to normal tissue, may, for example, be the amount of Thr51P HP1β which is higher statistically than the amount which is determined to be present in a biological sample obtained from the patient without treatment with the DNA damaging therapy.

A regimen which is found to be produce toxicological effects in the individual may be altered, for example by reducing the dosage, intensity or frequency of administration, to reduce or abolish the toxicological effects.

The methods described herein may be useful in optimising a treatment regimen for an individual. A method for optimising a regimen of treatment, in particular cancer treatment, with a DNA damaging therapy for an individual may comprise:
  (a) subjecting the individual to an initial regimen of DNA damaging therapy;
  (b) monitoring the level of Thr51P HP1β in the individual, wherein a change in the level or amount of Thr51P HP1β in response to the regimen is indicative that the regimen is optimised for the treatment of cancer in the individual.

In some embodiments, a change in the level of Thr51P HP1β beyond a pre-determined value or a change in the ratio of Thr51P HP1β in tumour relative to normal tissue is indicative that the regimen is optimised for the treatment of cancer in the individual. The change may be sustained over the duration of the regimen.

The initial regimen, e.g. the initial dosage, frequency of administration and duration of the DNA damaging therapy may be determined by a medical practitioner. If the initial regimen of the DNA damaging therapy is insufficient to cause a sustained change in the level or amount of Thr51P HP1β, the regimen may be altered or adjusted until the level of Thr51P HP1β in the individual changes. In some embodiments, if the initial regimen of the DNA damaging therapy is insufficient to change the level or amount of Thr51P HP1β beyond a predetermined value, the regimen may be altered or adjusted until the level of Thr51P HP1β in the individual is beyond the pre-determined value. A method may thus comprise the further steps;
  (c) altering the regimen of DNA damaging therapy and subjecting the individual to the altered regimen;
  (d) monitoring the level of Thr51P HP1β in the individual, and
  (e) repeating steps c) and d) until a change in the level of Thr51P HP1β is observed,
  wherein a change in the level or amount of Thr51P HP1β in response to the regimen is indicative that the regimen is optimised for the treatment of cancer in the individual.

The change may be sustained over the duration of the regimen.

In some embodiments, step (e) may comprise repeating steps c) and d) until the level or amount of Thr51P HP1β changes beyond a predetermined value, wherein a change in the level of Thr51P HP1β beyond the predetermined value is indicative that the regimen is optimised for the treatment of cancer in the individual.

The regimen may be altered by increasing one or more of the dosage, intensity, frequency of administration, and/or duration of the DNA damaging therapy. The skilled person is readily able to alter or modify the treatment regimen and monitor resultant Thr51P HP1β levels as described herein.

The toxicological effect of the increased dose regimen may be assessed in the individual. Toxicological effects may be assessed by a medical practitioner and determined to be acceptable or unacceptable in accordance with standard criteria. A regimen which is found to cause unacceptable toxicological effects in the individual may be altered, for example by reducing the dosage, to reduce or abolish the toxicological effects.

Another aspect of the invention provides an antibody which binds preferentially to Thr51P HP1β relative to HP1β which is not phosphorylated at Thr51.

Suitable antibodies are described in more detail above and may be useful in methods of assessing DNA damage in a cell, as described herein.

Another aspect of the invention provides a kit for assessing DNA damage in a cell, for example using a method described above, comprising:
an antibody as described herein and a
a secondary antibody which binds to said member and comprises a detectable label.

A kit may comprise reagents for determining the amount of Thr51P HP1β in a sample. For example, a kit may comprise one or more antibodies or other ligands for Thr51P HP1β and/or one or more detection reagents, including secondary antibodies, labels, and enzymatic substrates. A kit may, for example, comprise suitable reagents and materials for performing immunoassays, such as enzyme linked immunosorbent assays (ELISAs), immunoblotting, e.g. Western blots, or in situ hybridization, as described herein.

A kit may also include suitable means for detection, buffers, calibration and any other reagent for use in a protein peptide or nucleic acid assay. A kit may comprise one or more controls, standards or references for use in a test. The kit may comprise software for use in a method described herein.

Reagents may be sealed in a suitable container that protects its contents from the external environment.

A kit typically also comprises instructions for using the kit components in a method described herein.

HP1α displays a high level of identity with HP1β and has a conserved phospho-acceptor residue at Thr50. HP1α may also be used to assess DNA damage. The above disclosure relating to Thr51P HP1β therefore also applies mutatis mutandis to Thr50P HP1α. For example, another aspect of the invention relates to a method of assessing DNA damage in a cell comprising:
determining the level or amount of Thr50 phosphorylated HP1α protein in the cell.

The level or amount of Thr50 phosphorylated HP1α may be determined as described above, mutatis mutandis for Thr51P HP1β.

The amino acid sequence of human HP1α (GeneID 23468), for example, is available on the Genbank database under accession number NP_036249.1 GI: 6912292. The nucleotide sequence of human HP1α is available on the Genbank database under accession number NM_012117.1 GI: 6912291.

Various further aspects and embodiments of the present invention will be apparent to those skilled in the art in view of the present disclosure. All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures and tables described below.

FIG. 1 is a representation of the FRAP recovery curves (n=7) of EGFP-HP1β in euchromatin/nucleoplasm (EC) or heterochromatin (HC), before and after DNA damage by 10 Gy IR, fitted (solid lines) to a single component exponential (dotted lines show 95% CIs). Relative fluorescence intensity (RFI) is plotted on the vertical axis, against time in sec, on the horizontal.

FIGS. 2 and 3 show the FLIP decay curves (n=7) for EC and HC before and after DNA damage, defining the acceleration in mobility of the EGFP-HP1β protein post-damage. The solid lines represent a single order polynomial fit of the data.

FIG. 4 depicts the changes in the abundance and distribution of EGFP-HP1β immediately after the induction of laser induced DNA damage in a single HC focus (white circle). The area bounded by the orange square is enlarged below each panel.

FIG. 5 shows the FRAP curves for EGFP-HP1β in HC before and after DNA damage (n=10).

Figure 6:
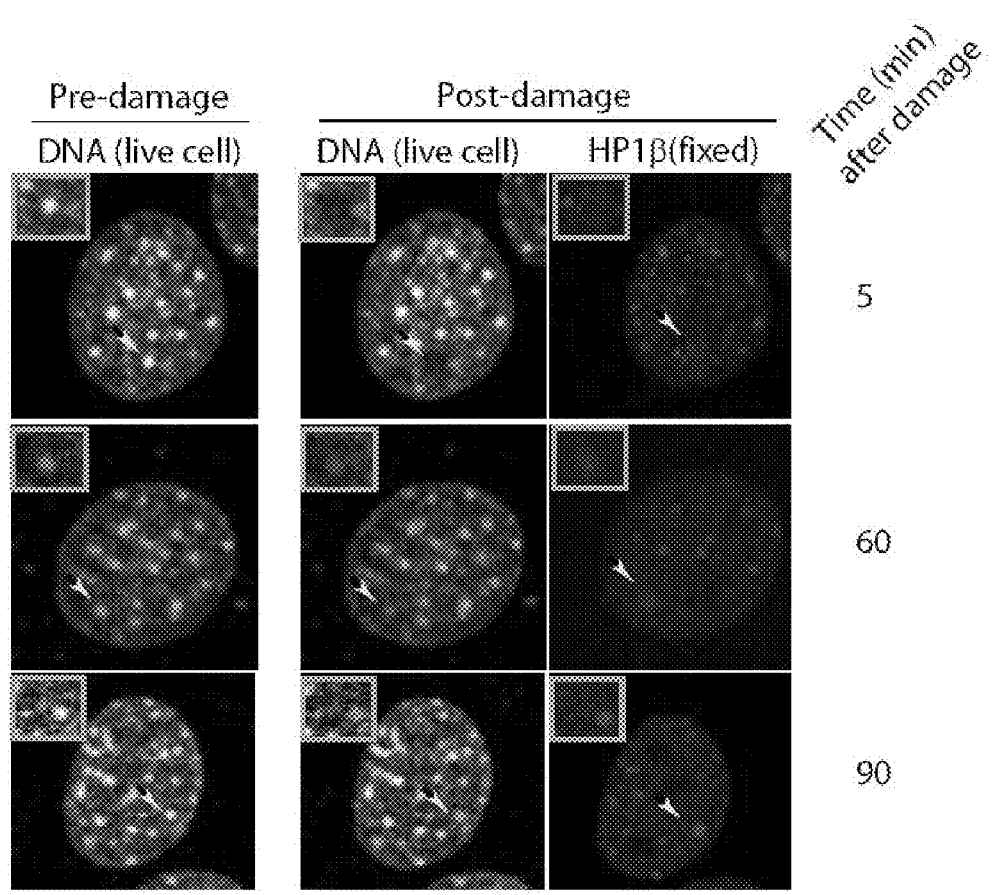

FIG. 6 shows changes in endogenous HP1β at defined time points (rows) after the induction of DNA damage to a HC focus. Hoechst staining of a live cell immediately prior to, and after, laser damage is shown in the first two columns. The third column shows the same cell after fixation and immunostaining for HP1β. The area marked by the arrow has been enlarged at the upper left corner of each frame. All results are typical of >3 independent experiments. Where shown, bars represent s.e.m.

FIG. 7 to 14 shows Thr51 substitution or phosphorylation alters the localization and dynamics of HP1β by disrupting a hydrogen-bond network essential for the HP1-H3K9me interaction.

Figure 7:
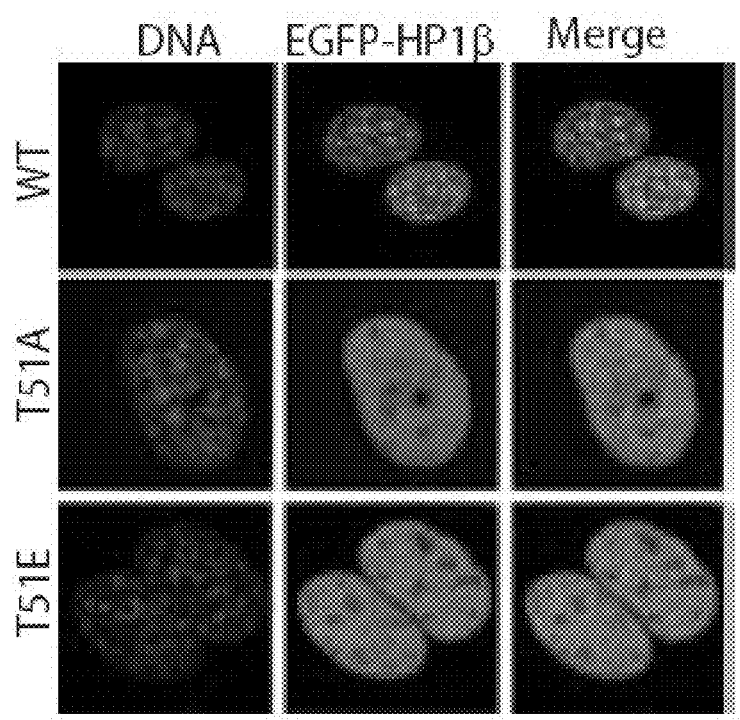

FIG. 7 shows the localization of wild-type (wt) EGFP-HP1β (top panel) or mutant forms in which Thr51 in the chromodomain has been replaced with alanine (T51A, middle panel)) or glutamic acid (T51E, bottom panel).

Figure 8:
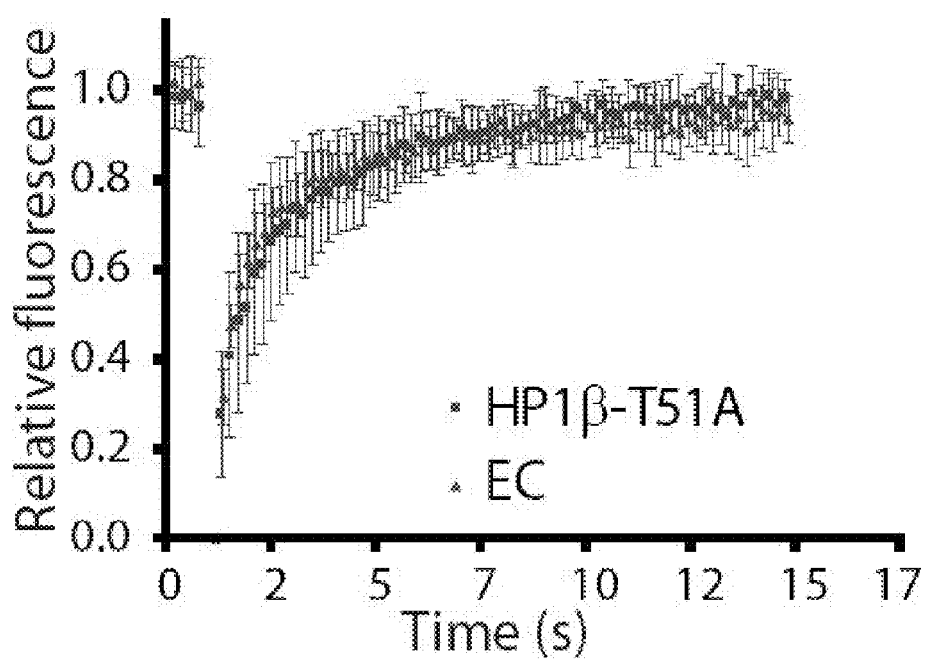

FIG. 8 shows that the dynamic behaviour of EGFP-HP1βT51A measured by FRAP is similar to the high mobility of EGFP-HP1β in EC regions. Fluorescence recovery (RFI, y-axis) after photobleaching is shown over time (n=10). Error bars represent s.d.

Figure 9:
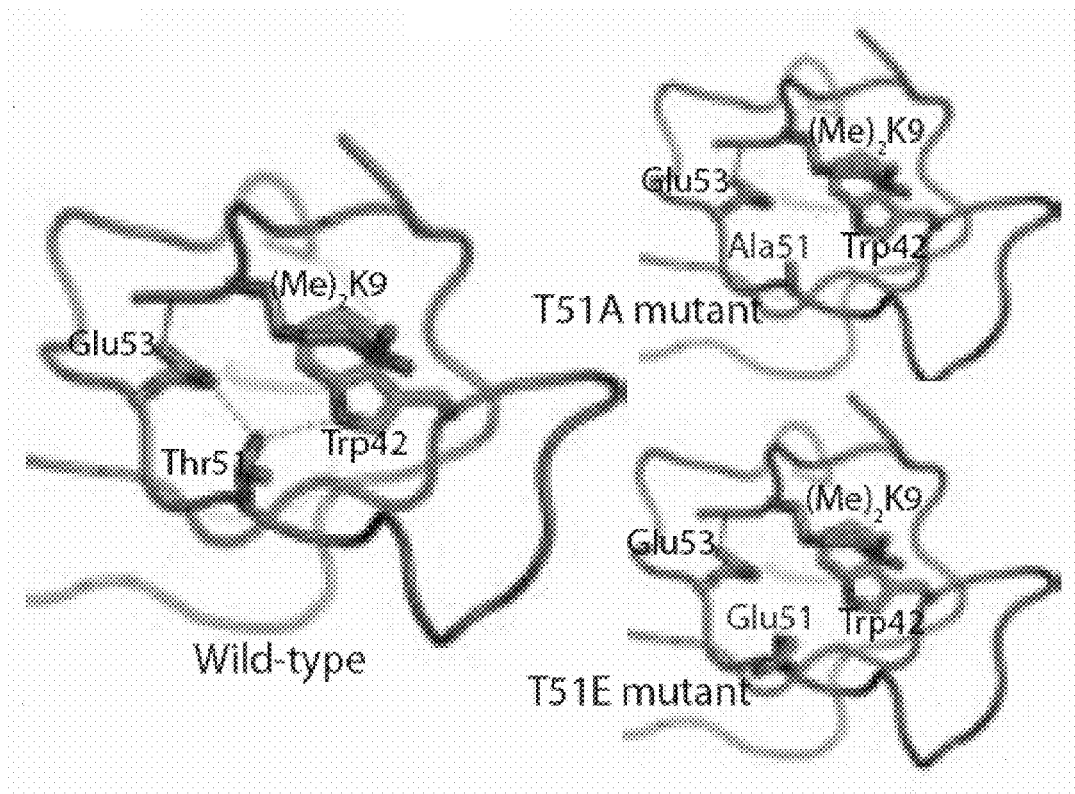

FIG. 9 shows a model for the interaction of the wild-type Hs HP1β chromodomain bound to methylated K9 of histone H3 ((Me)2K9), based on the PDB co-ordinates 1KNA, compared with its T51A and T51E mutants. A network of hydrogen bonds between the side chains of Glu53, Thr51 and Trp42 of the Hs HP1β chromodomain, marked as dashed lines, is disrupted in the T51A and T51E mutants.

Figure 10:
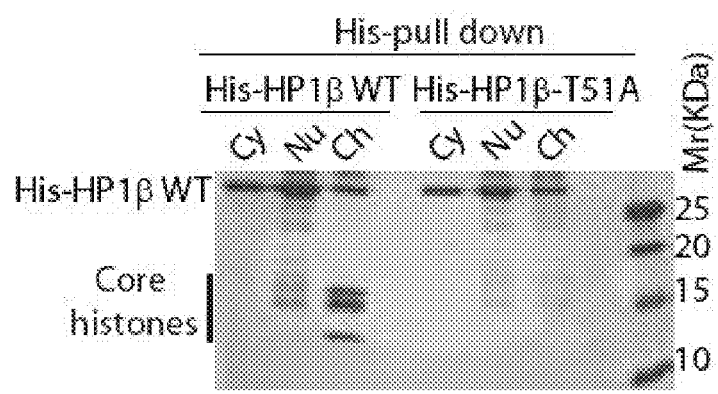

FIG. 10 shows Cy (cytoplasmic), Nu (nuclear soluble) or Ch (chromatin-bound) proteins pulled down with His-tagged HP1β wt or T51A mutant proteins in a Coomassie stained 12% SDS-PAGE gel. The identity of the four core histones, pulled down by the wt but not the T51A mutant protein, was confirmed by mass spectrometry.

Figure 11:

FIG. 11 shows a Western blot analysis of proteins pulled down with His-tagged HP1β wt, S70A or T51A mutant proteins in nuclear extracts. Blots were probed with antibodies against HP1β (top row), histone H3 (middle row) or histone H3K9-tri-me (bottom row). The S70A mutant, whose localization and dispersal after DNA damage are indistinguishable from the wt, serves as a control. All three variants equally pull down endogenous HP1β.

Figure 12:
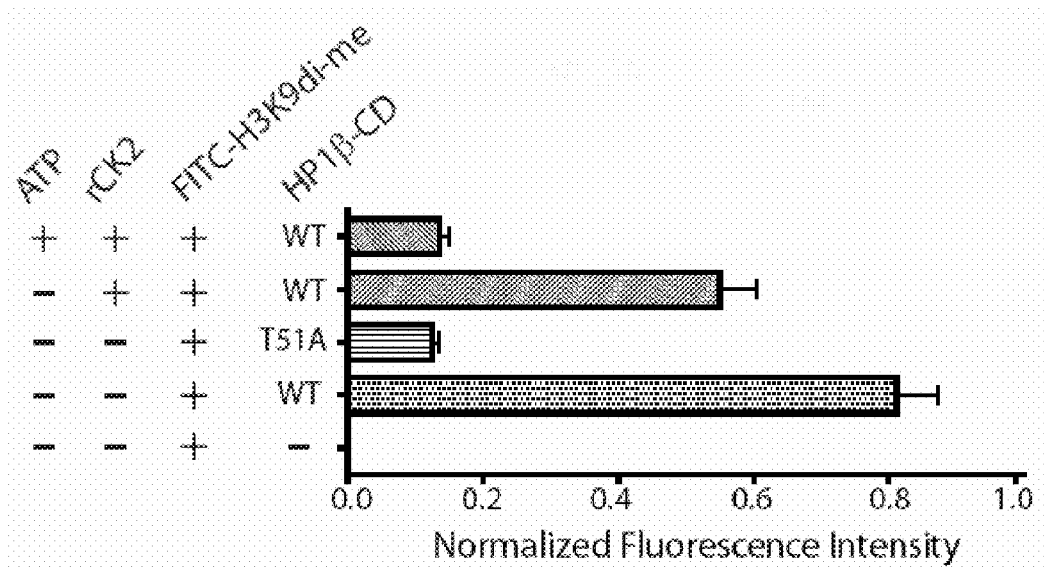
Figure 13:
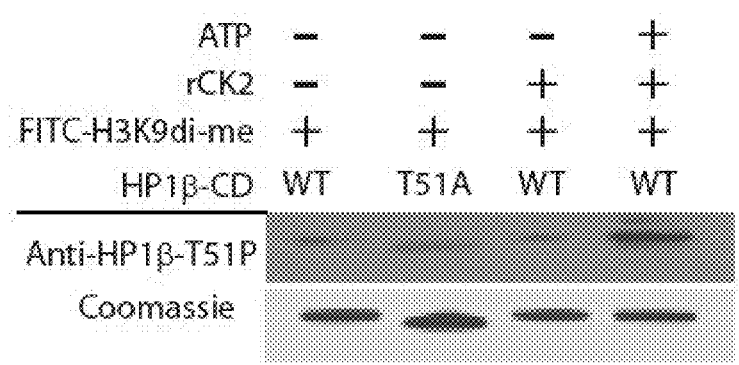

FIGS. 12 and 13 show that interaction of the HP1-chromodomain with methylated H3K9 is disrupted by CK2 phosphorylation on Thr51.

FIG. 12 shows the fluorescence intensities (x-axis) of a fixed volume of glutathione beads used to pull down a FITC-H3K9di-me peptide incubated with the different GST-HP1β chromodomain fusion proteins listed (n=3, error bars represent s.e.m). Decreased peptide binding (i.e. fluorescence intensity) occurs when the GST-HP1β chromodomain is phosphorylated on Thr51, as demonstrated in FIG. 13 by probing protein eluted from the glutathione beads with anti-HP1βT51P. Equal loading of GST-HP1β chromodomain in each track is shown by Coomassie staining.

FIGS. 14 to 17 show Thr51 phosphorylation is induced after DNA damage and accompanies HP1β dispersal from damage sites.

Figure 14:
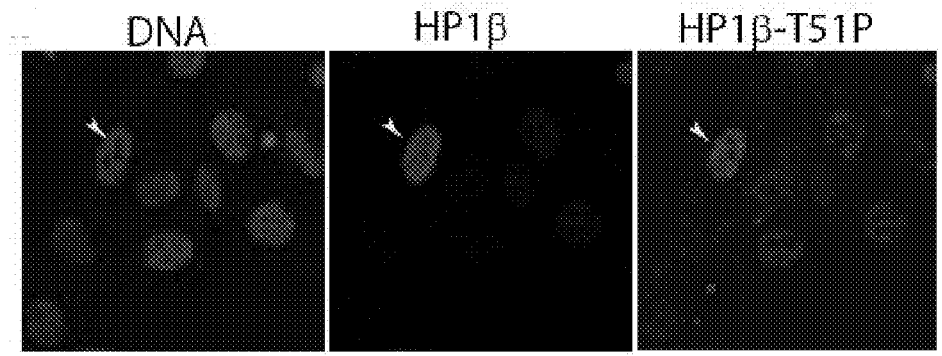

FIG. 14 shows U2OS cells treated 72 hrs after HP1β depletion with 20 μM etoposide for 1 hr before fixation. Nuclei (DNA) were stained with anti-HP1β and anti-HP1βT51P. HP1βT51P staining is diminished only in HP1β-depleted cells (light arrows).

Figure 15:
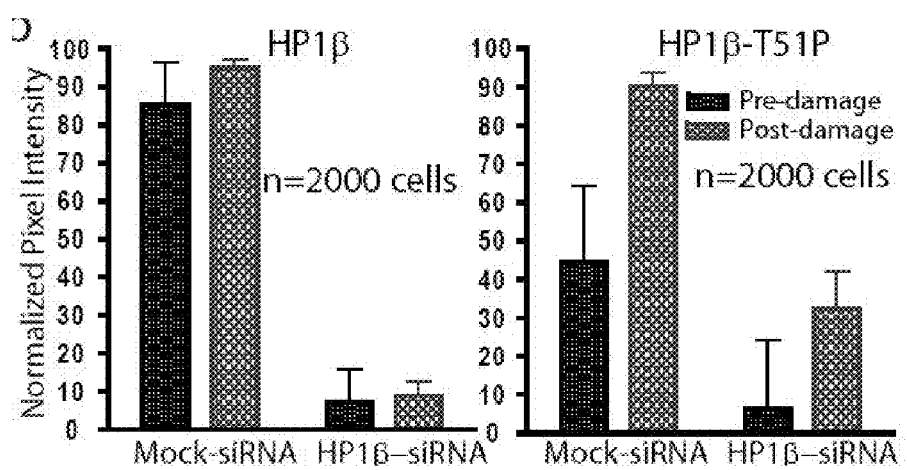

FIG. 15 shows immunofluorescence intensity per cell for HP1β (left) and HP1βT51P (right) after HP1β knockdown and etoposide treatment (n=2000, error bars represent s.d) measured with a Cellomics HCS microscope. Both the induction of anti-HP1βT51P staining after DNA damage in the Mock siRNA control, as well as a significant decrease of average HP1βT51P staining intensity per cell after HP1β depletion are evident.

Figure 16:
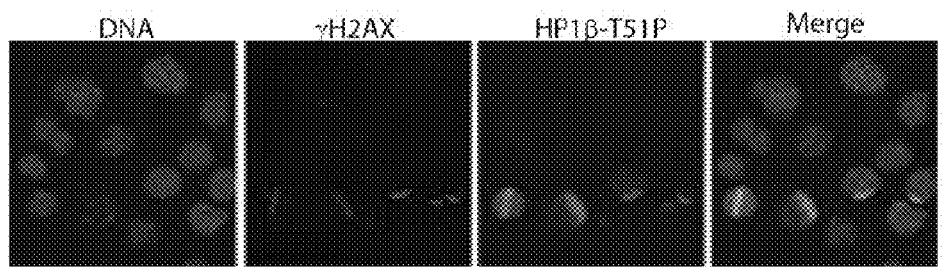

FIG. 16 shows a representative field of MEFs damaged by 405 nm laser micro-irradiation fixed and stained within 5 min post-damage. HP1βT51P staining is present only in damaged nuclei (DNA) marked by γH2AX formation.

Figure 17:
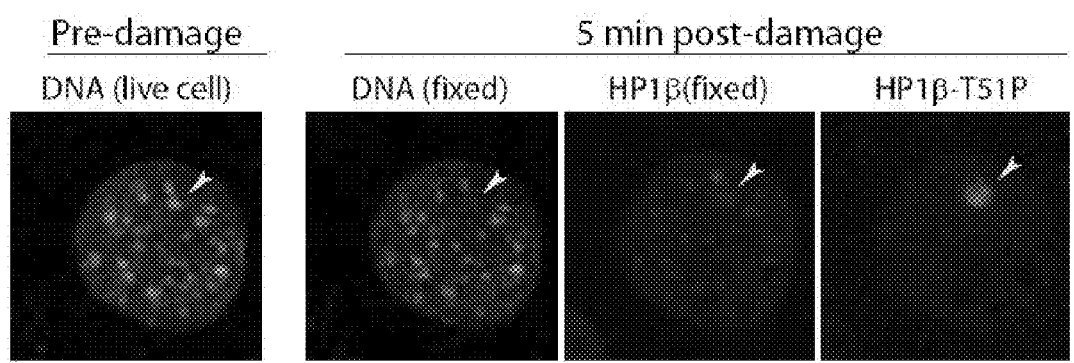

FIG. 17 shows the localized induction of anti-HP1βT51P accompanying HP1β dispersal in a single 405 nm laser-damaged HC focus (light arrow). The first panel is a live cell image of Hoechst staining prior to radiation showing the undamaged HC focus.

Figure 18:
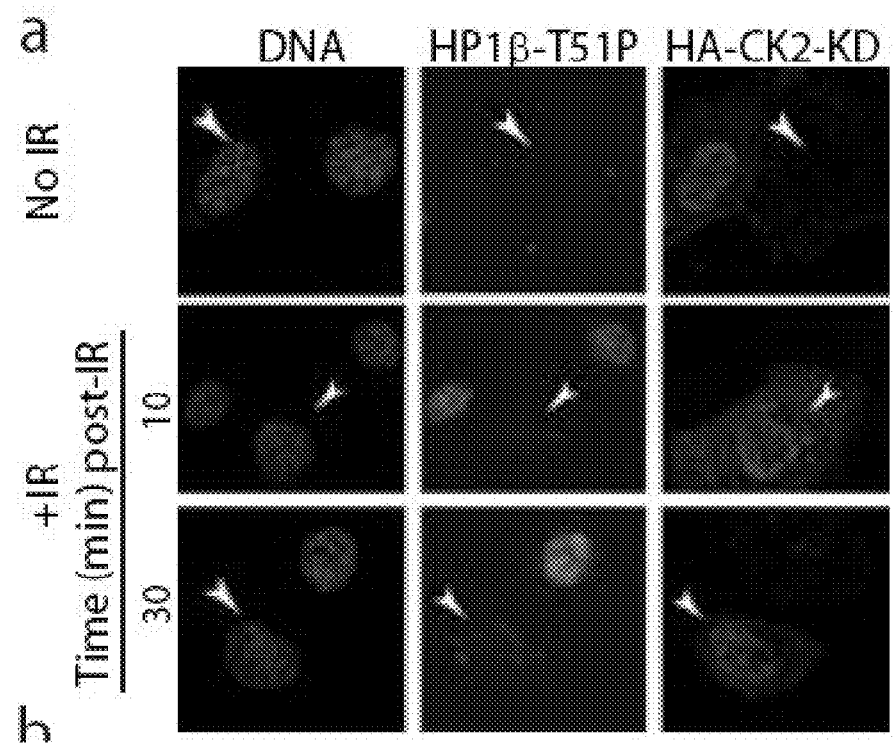
Figure 19:
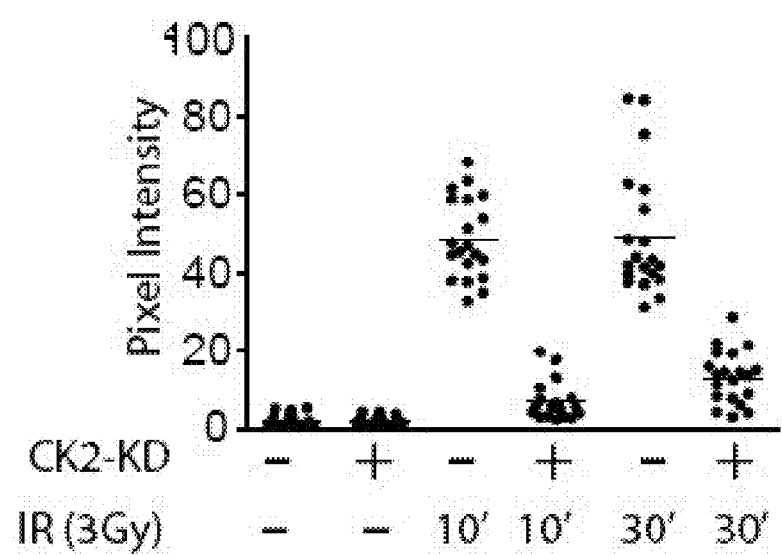
Figure 20:
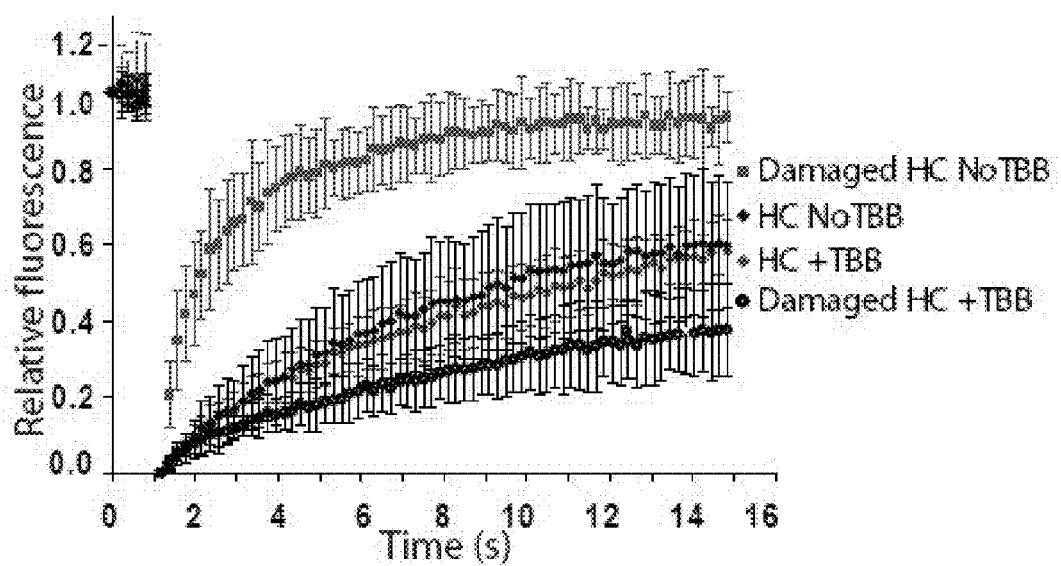

FIGS. 18 to 20 show that inhibition of CK2 suppresses the phosphorylation of HP1β on Thr51 and mobilization after DNA damage.

FIG. 18 shows MEFs (nuclei stained) transfected with an HA-epitope tagged, kinase-dead (KD) K69M CK2α' mutant. Dark anti-HA staining marks the transfected cells, whereas anti-HP1βT51P staining is light. Transfected cells (arrowheads) have less HP1βT51P staining after 3Gy IR compared to neighbouring, untransfected cells.

FIG. 19 is a quantitative representation of anti-HP1βT51P staining intensity per cell under the specified experimental conditions (n=30, p<0.05 by ANOVA/Dunnet's).

FIG. 20 compares the dynamic behaviour of EGFP-HP1β after DNA damage, with (black circles) or without (light) preexposure to 75 μM of the CK2 inhibitor, TBB.

FIG. 21 to 24 shows HP1β mobilization by CK2 promotes H2AX phosphorylation.

Figure 21:
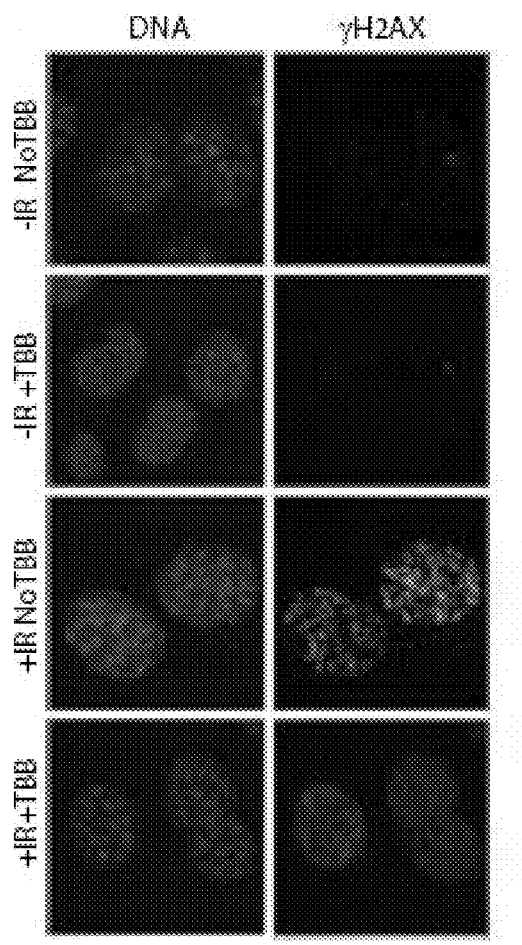

FIG. 21 shows that pre-exposure of MEFs to 75 μM TBB suppresses γH2AX foci formation at 5 min after 3 Gy IR. DNA is stained blue, and γH2AX, green. Rows i and ii show undamaged cells without (−IR NoTBB) or with (−IR+TBB) pre-exposure; while rows iii and iv represent IR damaged cells without (+IR NoTBB), or with TBB pre-exposure (+IR+TBB).

Figure 22:
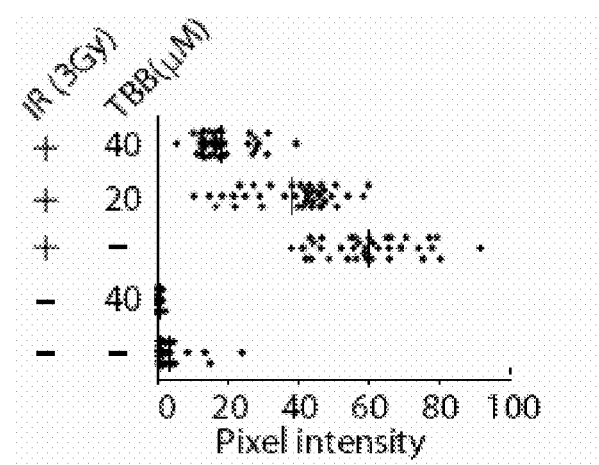

FIG. 22 shows a dot-plot showing that the pixel intensity of γH2AX staining after damage under identical imaging conditions is reduced in a dose-dependent manner by TBB pre-exposure (n=20 per sample, p<0.01, independent t-tests).

Figure 23:
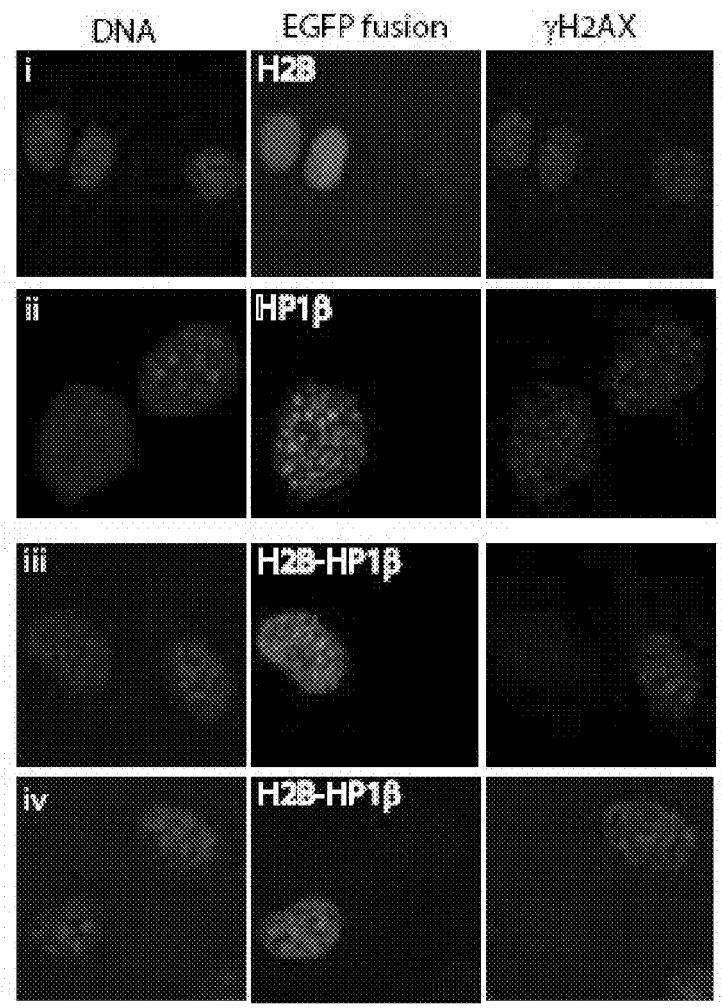

FIG. 23 shows that an EGFP-H2BHP1β fusion protein constitutively immobilized on chromatin suppresses γH2AX foci formation at 5 min after 3 Gy IR. DNA is stained blue, the different EGFP fusion proteins, green, and γH2AX, red. Rows i and ii show MEFs transfected with constructs encoding EGFP-HP1β or H2B-EGFP, whereas rows iii and iv both show H2B-EGFPHP1β. Untransfected cells within the same field provide an internal control.

Figure 24:
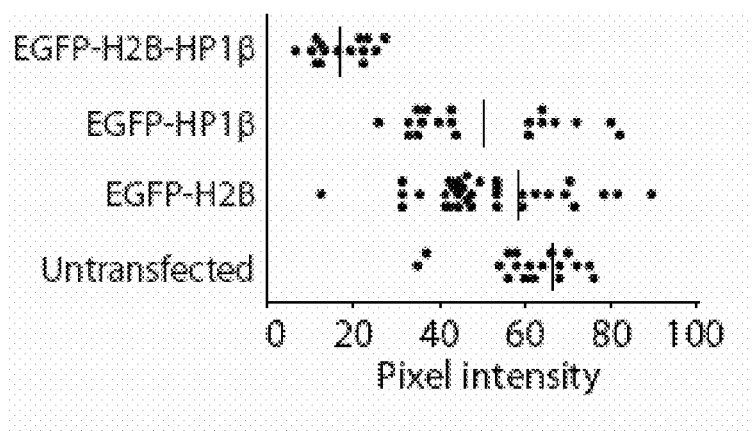

FIG. 24 shows a dot-plot representing the pixel intensities of γH2AX signal per cell under identical imaging conditions for cells with and without the transfected constructs (n=20, p<0.05 with t-test/ANOVA for multi-group comparison).

Figure 25:
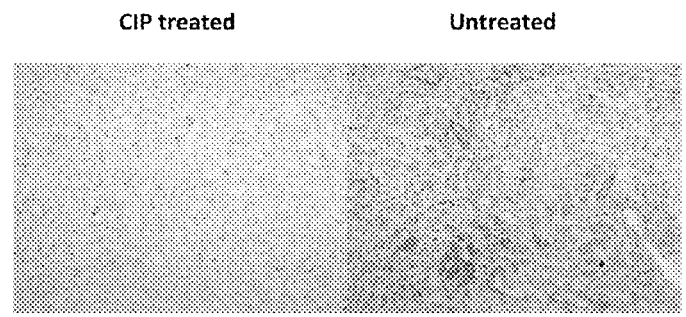

FIG. 25 shows the binding of the pT51 antibody to untreated samples and samples treated overnight with Calf intestinal Phosphatase (CIP).

Figure 26:
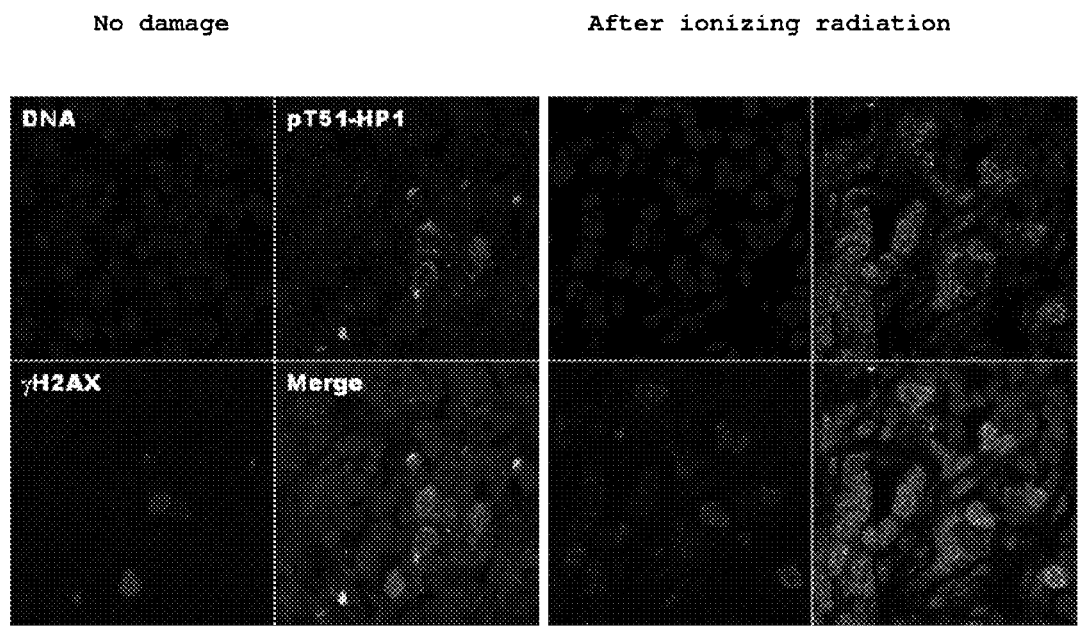

FIG. 26 shows the co-staining of irradiated and non-irradiated mouse tissue with gH2AX and pT51 antibodies.

EXPERIMENTS

Material and Methods

FRAP and FLIP Assays

MEFs were seeded in 2-well Lab-Tek chambers (Nunc) after transfection with the EGFP-HP1β construct. Before imaging, growth medium was replaced with phenol-red free L15 imaging medium. Live cell imaging and photobleaching experiments were performed using a 40× 1.2 NA water immersion lens on a Zeiss LSM 510 Meta confocal microscope (using a heating chamber to maintain the cells at 370 C) with the 488 nm line of an Argon laser operating at 6.1 A.

FRAP analysis was performed by a method previously established in our lab 27. For low-bleach FRAP (see FIG. S1), selected regions of HC and EC were simultaneously bleached in a diffraction-limited spot with a pulse of 2 iterations at 100% of the 15 Mw 488 nM Ar laser. Post-bleach images were acquired at a lower frequency of an image every 400 msec. Image bleach was corrected separately for EC and HC regions using a nearby unbleached cell. For high-bleach FRAP experiments, photobleaching was with 35 iterations at the same laser output, and images were collected every 290 msec. The normalized curves were plotted in GraphPad Prism, and recovery curves were fitted to a single order exponential equation $Y=Ymax*(1-\exp(-K*X))$ to yield a recovery constant K; shown to be different among groups by the sum of squares f-test at p<0.05.

Transfected cells for analysis were chosen under epifluorescence. Transfection levels were controlled by using cells of similar nuclear size, that were visible but not saturated, at a fixed imaging intensity (1% transmission at maximal scan speed and fixed PMT gain at an optical slice of 1.5 microns). An integrative time-bleach series was set up to take five initial images, then bleach a 2×2 μM square with 30 iterations of 100% laser intensity in an EC region every 4 images, for a total of 200 images. The cells were imaged with a fixed 7× zoom and fixed bleach ROI size in a 512×512 pixel image window to keep the time between images constant for different cells to allow comparison. Circular regions of HC and EC of similar size (1 μM radius) equidistant at 10 μM from the site of bleaching were then chosen, and the pixel intensities during the FLIP procedure recorded. The procedure was performed on control and irradiated cells (10 min after IR to allow temperature equilibration and decreased drift during scanning); with control cells also kept at room temperature for 20 min to compensate for the irradiation process. Nearby imaged, but unbleached, cells were used to correct for the effect of imaging during the FLIP procedure. For the data analysis, the raw pixel intensities were transferred into GraphPad Prism, and converted into relative intensities as a percentage of the mean of the first three values. These intensities were plotted across time to generate the FLIP decay curves with standard errors being calculated from multiple measurements (n=7, in repeated experiments, limited to avoid discrepancies from changes in time after irradiation). The curves were fit to a single order polynomial equation y=a+bx and the decay constant b shown to be statistically different for different groups at $p<0.05$ using the f-test.

Laser Micro-Irradiation

Laser micro-irradiation was used to induce DNA damage by modifying a previously described method[28]. Briefly, cells were grown on chambered, 1-thickness borosilicate glass cover slides (Nunc), incubated with 10 μg/ml Hoechst dye 33342 for 5 min at 37° C., washed twice with Leibovitz's L-15 Medium (Gibco), and further incubated in this medium. Cells were imaged using a Zeiss LSM 510 Meta inverted confocal microscope fitted with a heated stage unit for live-cell imaging (heating insert P, Zeiss). HC or EC regions, selected based on EGFP-HP1β localization, were damaged by applying 200 iterations of 100% power from the 405 nm line of a 15 mW Ar laser. To monitor changes, serial time-lapse images were taken at 256×256 pixel 8-bit resolution with a scan speed of 293 msec, using the 488 nm line from the Ar laser at 1% power. For some experiments, cells were fixed at the indicated times for staining and immunofluorescence.

A pulsed N2 laser system with a 365 nm dye cell (Micropoint; Photonics systems) coupled to the epifluorescence path of a Zeiss-510 LSM Confocor2 was also used for DNA damage experiments to induce localized damage in a large number of cells. The cycling time was set at approx 10 Hz and the power used to excite Hoechst for DNA damage (calibrated by γH2AX staining) was set at maximal attenuation of laser output through the supplied gradient neutral density filter (approx 75%). Cells visualized under phase contrast were moved by manual operation of the motorized stage through a fixed point of laser illumination to induce stripes of DNA damage across several nuclei.

Typically, 100-200 cells were damaged per experiment, and then fixed for immunofluorescence.

Immunofluorescence

Cell staining and immunofluorescence analyses were carried out as described previously[2]. Briefly, transfected and untransfected cells were grown on coverslips and subjected to different treatments as indicated in the text prior to fixation. Cells were fixed using 4% formaldehyde for 10-15 min, followed by solubilisation and blocking with 3% BSA in 1×PBS, 0.05% Tween-20, 0.05% Triton. Imaging was performed on a Zeiss LSM510 Meta confocal microscope, using a 40× objective with fixed optical slice, laser power and detector/amplifier settings for all samples across each individual experiment to allow comparison. Quantitative analysis for HP1βT51P and γH2AX staining was performed using mean per-nucleus intensity to avoid any discrepancy in the definition or counting of foci. This was performed on identically stained and imaged samples by estimation of raw pixel intensity values for a defined number of cells, specified for each experiment, through the Zeiss LSM software, and comparison of the different groups by one-way ANOVA and Dunnet's post test. High content microscopy was also used for certain experiments; 96 well plates (Nunc) with cells seeded at 3000/well were treated with specified DNA damaging agents, pre-treatments/siRNA, then fixed and immunostained. The plates were imaged and analyzed using a Cellomics high content screening microscope, using a 40× non-immersion objective. Hoechst staining was used for object identification and the average intensity of fluorescent signal per nucleus was estimated using the target activation Cellomics bio-application. 500 cells were analysed per well, and standard errors calculated from an average of the means of 8 wells.

Expression and Purification of HP1β

Full-length human HP1β or its chromodomain were expressed in *E. coli* BL21 (Stratagene) as carboxyl-terminal fusions to GST using the pGEX4T3 vector (Pharmacia). Bacteria expressing the fusion protein were lysed in phosphate-buffered saline (PBS) supplemented with 5 mM DTT, 0.5% NP40 and protease inhibitors, and the soluble fraction was applied onto glutathione-Sepharose 4B beads (Amersham). After extensive washing, Full-length HP1β and the chromodomain fragment were cleaved from the GST moiety using thrombin protease (Amersham) in PBS buffer at 22° C. for 16 hr. Thrombin was removed from the sample by chromatography with benzamidine-Sepharose 4B (Amersham).

Peptide Synthesis and Binding Assay

A peptide (FITC-H3K9di-me) encoding residues 1-15 of the H3 tail dimethylated on Lys9 and N-terminally labelled with fluorescein was synthesised by Pepceuticals Limited, Nottingham, England. Ten μg of purified GST-HP1β chromodomain (or its T51A mutant form), 3 nmoles of FITC-H3K9di-me peptide (representing a 10-fold molar excess over HP1) and 20 μl of 50% GST bead slurry were added to a PBS based binding buffer containing 0.2% NP-40 and 0.1% BSA, and incubated at room temperature for 1 hr. For phosphorylation experiments, 25 μl of a kinase reaction containing 10 μg GST-HP1β chromodomain protein, 5000 units rCK2, in CK2 buffer containing 50 μM ATP, was used in place of the purified protein prep. After binding, the mixture was centrifuged at 5000×g for 3 min and all supernatant removed by gentle aspiration. The beads were resuspended in 50 μl binding buffer, transferred to assigned wells of a 96 well plate, and fluorescein fluorescence intensity read using a Fusion microplate reader (PerkinElmer, USA). A mixture of FITC-H3K9di-me and beads alone was used to calibrate background binding, to which the rest of the data were normalized before export to GraphPad Prism to calculate mean intensities and standard errors from different runs (n=3). Changes in binding were shown to be significant using a student's t-test.

Results

Figure 1:
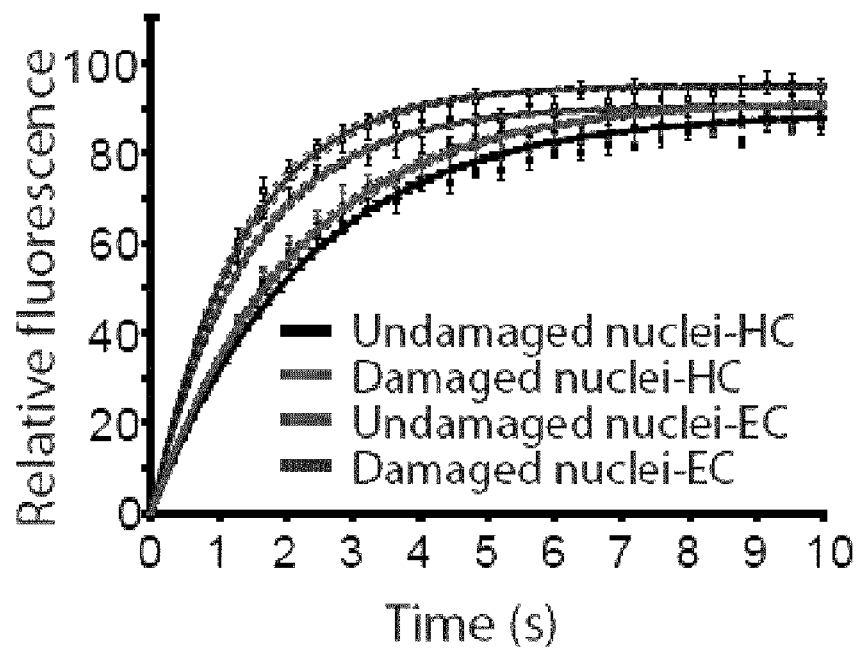
FIGS. 1 to 6 show alterations in HP1β dynamics and localization accompany its mobilization after DNA damage.

An EGFP-HP1β fusion protein[7-9] was used to monitor changes in the dynamic behaviour of HP1β after DNA breakage. In undamaged cells, fluorescence recovery after photobleaching (FRAP), using a range of laser-light intensities, shows that EGFP-HP1β exhibits distinct molecular mobilities in euchromatin (EC) versus heterochromatin (HC)[7,8]. Exposure of cells to ionizing radiation (IR) alters the dynamics of EGFP-HP1β FRAP in a statistically significant manner (FIG. 1).

Recovery in both EC and HC occurs more swiftly as evinced by a change in the association constant, K, calculated from a single component exponential fit for the FRAP curves. Similar changes are induced by the clastogenic drug etoposide. Therefore, HP1β mobilization is not solely a response to IR.

Figure 2:
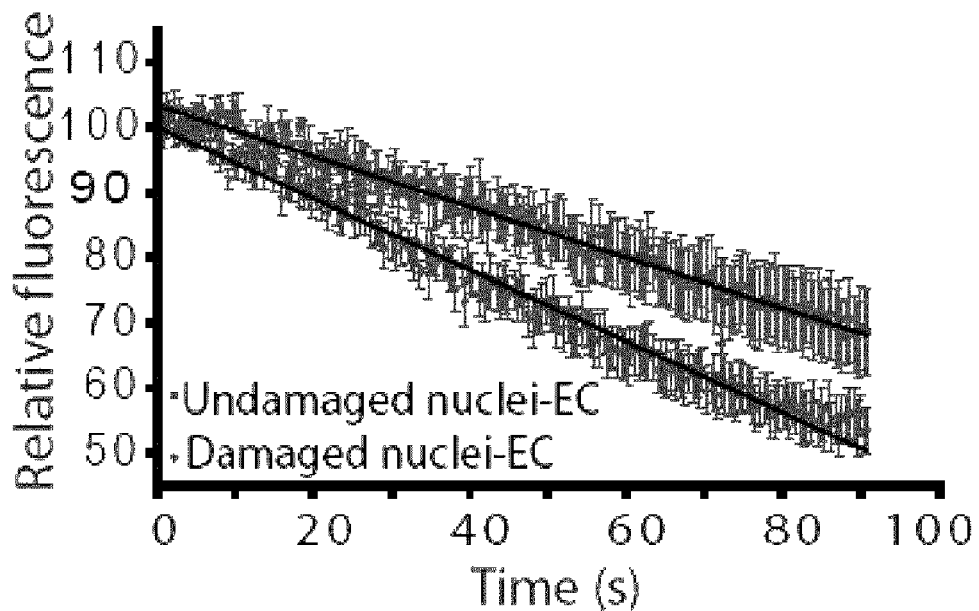
Figure 3:
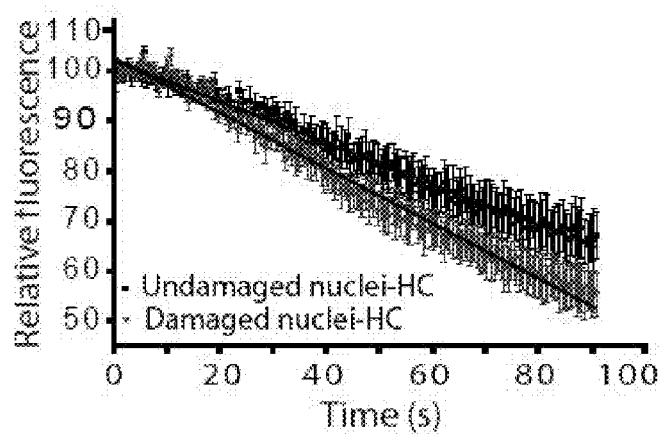

EGFP-HP1β mobilization after DNA damage in EC, besides HC, is evident using fluorescence loss in photobleaching (FLIP), which measures the exchange of fluorescent molecules between distinct regions within a cell, and thus, their relative diffusional mobility, provided imaging and bleaching parameters are held constant. The changes in FLIP dynamics of EGFP-HP1β after exposure to IR are equivalent in EC and HC, with the best-fit decay constant increasing from 0.4+0.01 (s.e.m.) to 0.55+0.01 in each (p<0.05, n=7, t-test), confirming exchange between the two compartments and suggesting that a similar mechanism causes mobilization in both (FIGS. 2, 3).

Figure 4:
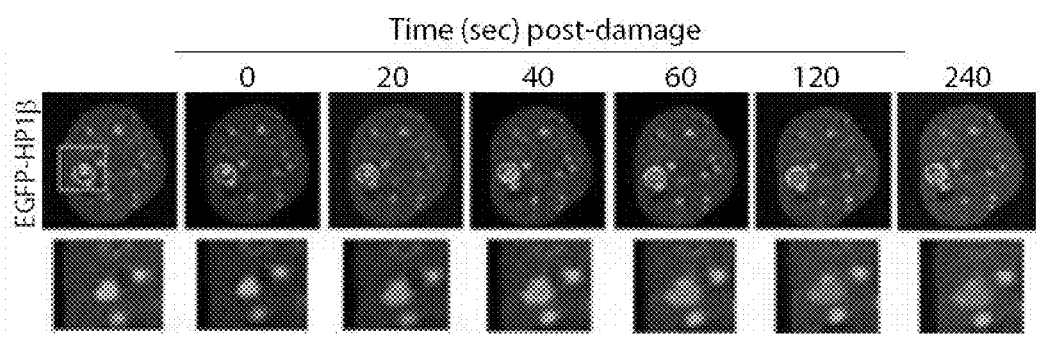
Figure 5:
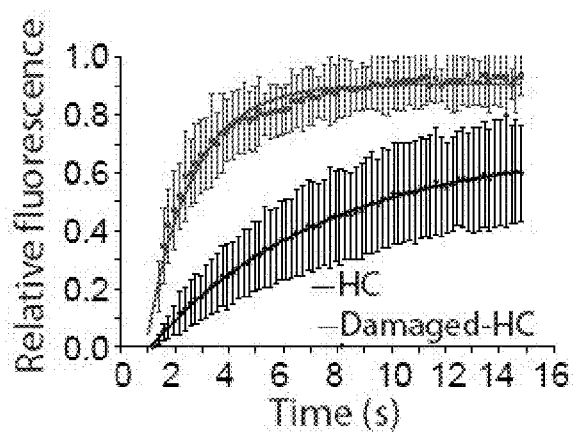

We precisely targeted DNA double-strand breaks (DSBs), marked by γH2AX formation and 53BP1 recruitment, to specific living cells or discrete regions within a single nucleus, using a 405 nm laser11. Damage to a single HC focus (FIG. 4, circled white) swiftly disperses EGFP-HP1β, inciting local rearrangement and spreading within 20 sec (FIG. 4), but with little overall variation in DNA staining, distinct from reported changes in GFP-histone H2B 12. The FRAP dynamics of EGFP-HP1β changes locally at damage sites (FIG. 5). Endogenous HP1β visualized by immunofluorescence is also rearranged and dispersed from a damaged HC focus within 5 min after DNA damage, to gradually re-accumulate over 90 min (FIG. 6), consistent with a physiological response to DNA breakage and repair.

HP1β localizes to chromatin via its direct interaction with H3K9me. Unexpectedly, neither the distribution nor abundance of H3K9-tri-me staining is altered after DNA damage. This is also true for histone H3 tri-methylation on lysine 4 (H3K4-tri-me), histone H3 acetylation on lysines 14 or 18 13, or histone H4 on lysine 16. Thus, it seems unlikely that alterations in the histone code mobilize HP1β after DNA damage. Instead, mobilization may result from changes in HP1β itself.

Substitution of eight putative phosphorylation sites in HP1β affected neither the localization nor the damage-induced dispersal of EGFP-HP1β from heterochromatic foci. By contrast, alteration of Thr51 in the HP1β chromodomain either to Ala or to Glu (respectively expected to preclude, or mimic, phosphorylation) suffices to distribute mutant EGFP-HP1β diffusely throughout the nucleus (FIG. 7), and to confer rapid dynamics in FRAP (FIG. 8). Similarly, replacement of the corresponding residue, Thr50, in human HP1α excludes HP1α from heterochromatin.

Thr51 is evolutionarily conserved. The structure of the HP1β chromodomain (FIG. 9), modelled from a Dm HP1-H3K9me complex 16, reveals that the hydroxyl moiety in the Thr51 side-chain participates in a hydrogen-bond network essential for complex formation. Phosphorylation or replacement of Thr51 is expected to disrupt this hydrogen-bond network (FIG. 9), diminishing the capacity of HP1β to bind to chromatin via H3K9-tri-me. Indeed, whereas His tagged HP1β (His-HP1β) effectively pulls down the four core histones from cell extracts (FIG. 10), mutant His-HP1βT51A does not. Moreover, His-HP1β and its Ser70Ala mutant both bind efficiently to histone H3K9-tri-me from chromatin, although mutant His-HP1βT51A does not (FIG. 11). Thus, Thr51 modification suffices to release HP1β from chromatin, although additional, DNA damage induced changes could also assist.

In human HP1, Thr51 lies within an atypical phospho-acceptor site for CK2[17], divergent from the consensus Ser/ThrXXAsp/Glu. Indeed, recombinant (r) CK2 can phosphorylate the wild-type (wt) HP1β chromodomain (but not its T51A mutant form) confirming that this residue is a specific target.

The production and validation of an antibody specific to the phosphopeptide SDEDN(phosphoThr)WEPEEC is described in Ayoub et al. 2008. The antibody was found to react in vitro with recombinant HP1β wt protein, solely after exposure to rCK2, but not with the T51A mutant. In vivo, the antibody reacts with the wild-type but not the mutant protein. This reactivity increases after etoposide-induced DNA damage, with kinetics parallel to γH2AX formation.

Phosphorylation of the HP1β chromodomain on Thr51 by rCK2 releases it from binding to a fluorescein-tagged H3K9di-me peptide (FIG. 12). The fluorescent peptide is pulled down by the HP1β chromodomain, but not by its T51A mutant. Thr51 phosphorylation by rCK2 diminishes binding of the fluorescent H3K9 me peptide to background levels. In cells treated with isoform-specific short, interfering (si)RNAs for HP1β, diminished HP1β expression corresponds with diminished anti-HP1βT51P staining after etoposide induced DNA damage (FIGS. 14, 15). IR also elicits an increase in anti-HP1βT51P staining, inhibited by pre-incubation with the phosphopeptide immunogen. There is increased nucleoplasmic and local staining for HP1β-T51P specifically in damaged nuclei marked by γH2AX phosphorylation, and not in undamaged ones, after laser-irradiation at 405 nm (FIG. 16) or 365 nm. Laser damage to a HC focus triggers dispersal of endogenous HP1β accompanied by spreading HP1β-T51P staining around the damaged region (FIG. 17).

Together, these findings suggest that HP1β-T51P is created locally in damaged chromatin and thereafter released, mirroring the pattern of HP1β rearrangement and dispersal.

Inhibition of CK2 activity by chemical or genetic means suppresses damage-induced changes in HP1β dynamics and its phosphorylation on Thr51. In cell extracts, anti-HP1βT51P detects a species with mobility corresponding to HP1, enhanced in a dose-dependent manner by etoposide treatment. Chemical inhibition of CK2 with 4,5,6,7-tetrabromo-benzimidazole (TBB) at 75 μM for 6 hrs, a concentration required to suppress CK2 activity in living cells[18], diminishes both the background detection and etoposide-induced enhancement of HP1βT51P levels. Genetic suppression of CK2 activity by an overexpressed dominant-negative form of the enzyme[19] is enough to suppress Thr51 phosphorylation after DNA damage (FIGS. 18, 19) Finally, TBB suppresses in living cells the changes in FRAP dynamics (FIG. 20) usually triggered by DNA damage.

Together, these observations demonstrate that CK2 mediates the mobilization of HP1β from chromatin after DNA breakage via Thr51 phosphorylation. Chromatin alterations may accompany PIK activation[20, 21], or modulate γH2AX deposition along chromosomes[12, 22, 23], but whether they help to trigger the response to DNA breaks is unknown. We not only find that CK2 inhibition suffices to diminish histone H2AX phosphorylation after DNA breakage (FIGS. 21, 22), but also that immobilization of HP1β on chromatin suppresses γH2AX formation.

We fused EGFP-HP1β to the histone H2B in a strategy previously used to render proteins constitutively chromatin-bound[10] whether before or after DNA damage. The intensity of γH2AX staining after DNA damage is inhibited in cells expressing the immobilized H2B-EGFP-HP1β fusion protein (FIGS. 23, 24).

Neither EGFP-HP1β nor H2B-EGFP (FIGS. 23, 24) expression to similar levels affects γH2AX staining, ruling out that this effect is merely the result of HP1β over-expression, or high levels of chromatin-bound H2B. Instead, our findings collectively show that mobilization of HP1β from chromatin facilitates H2AX phosphorylation after DNA damage.

Standard immunohistochemistry was performed on mouse tissue using the pT51 antibody. A conventional IHC protocol was used on pancreatic tissue/tumour which was formalin fixed and paraffin embedded. Antigen extraction was done using citrate acid buffer and microwaving. A nuclear antigen was found to be stained by the pT51 antibody.

The specificity of the antibody for a phosphorylated pT51 antigen was demonstrated by comparing the staining of specimens subjected to overnight treatment with Calf intestinal Phosphatase (CIP), with untreated specimens. A significant reduction in immunohistochemical staining was observed after CIP treatment (FIG. 25), confirming the phosphate specificity of the pT51 antibody.

To confirm whether the pT51 antibody recognises DNA damage in tissue, tissue specimens (pancreatic tumour and adjacent normal tissue) isolated from mice were immediately transferred into a DMEM growth media to maintain viability of cells. The specimen was divided into two, one half irradiated (10Gy) and the other left undamaged as a control. After 1 hour at 37° C., these tissues were fixed in formalin and paraffin embedded. Slides made from these sections were then co-stained with gH2AX and pT51 to establish whether the pT51 antibody specifically recognized DNA damaged cells. Fluorescent secondary antibodies (with confocal imaging) were used to improve sensitivity of detection.

The results are shown in FIG. 26. The increase in the number of cells that stain with gH2AX confirms the induction of DNA damage after ionizing radiation (as gH2AX is an established marker for DNA damage). The concomittant increase in signal intensity from the pT51 stain, and the fact that many of the cells that stain with gH2AX also stain with pT51 is indicative that a pT51 antibody works as a reagent to detect DNA damage in tissue sections.

We propose that dynamic alterations in chromatin structure triggered by HP1β mobilization promote H2AX phosphorylation, so far the earliest known event in the response to chromosomal breakage. Importantly, HP1β mobilization after DNA damage provides an unusual example of a mechanism that alters chromatin organization by targeting a histone-binding protein, rather than the histone code itself[26]. Such a mechanism could facilitate both the rapid remodelling of chromatin after DNA damage, as well as its efficient reversal by HP1β de-phosphorylation.

The results set out herein show that pT51 may be useful as a marker for DNA damage, with potential for clinical application. The significance of activation of the DNA damage response in carcinogenesis is shown in various reports e.g. Gorgoulis et al., 2005. Markers of such activation events are useful in the clinical setting for diagnosis, prognosis and predictive response to therapy (Bonner et al., 2008; Lobrich et al., 2005; Sedelnikova and Bonner, 2006).

Sequences:

```
Human HP1β
                                                              (SEQ ID NO: 1)
  1 mgkkqnkkkv eevleeeeee yvvekvldrr vvkgkveyll kwkgfsdedn twepeenldc 61 pdliaeflqs qktahetdks eggkrkadsd sedkgeeskp kkkkeesekp rgfarglepe 121 riigatdssg elmflmkwkn sdeadlvpak eanvkcpqvv isfyeerltw hsypsedddk 181 kddkn
```

TABLE 1

| | Bleomycin |
|---|---|
| ABVD | doxorubicin + Bleo + vinblastine + dacarbazine |
| ABV | doxorubicin + Bleo + vinblastine |
| BCD | Bleomycin + cyclophosphamide + dactinomycin |
| BEACOPP | bleomycin + etoposide + doxorubicin + cyclophosphamide + vincristine + procarbazine + prednisone |
| BEC | cisplatin + epirubicin + Bleo |
| BEP | Bleo + etoposide + cisplatin |
| BIP | Bleo + Cisplatin + ifosfamide |
| CMB | cisplatin + methotrexate + bleomycin - or - bleo + methotrexate + folinic acid + cisplatin |
| CHOP-B | cyclophosphamide + doxorubicin + vincristine + prednisone + bleo |
| COPP-ABVD alternating | cyclophosphamide + vincristine + procarbazine + prednisone + doxorubicin + bleomycin + vinblastine + dacarbazine |
| JEB | etoposide + carboplatin + Bleo |
| MOPP/ABV hybrid | Nitrogen mustard + vincristine + procarbazine + prednisone + doxorubicin + bleomycin + vinblastine |
| PACEBOM | prednisolone + doxorubicin + cyclophosphamide + etoposide + bleomycin + vincristine + methotrexate |
| POMMB/ACE | vincristine + methotrexate + folinic acid + bleomycin + cisplatin then dactinomycin + cyclophosphamide + etoposide |
| PBF | cisplatin + Bleo + 5-FU |
| PVB | cisplatin + vinblastine + Bleo |
| Stanford V | doxorubicin + vinblastine + nitrogen mustard + vincristine + bleomycin + etoposide + prednisone |
| | Etoposide (Vepesid ®, Etopophos ®, Epsin ®) |
| ADE | daunorubicin + cytarabine + etoposide |
| BEACOPP | bleomycin + etoposide + doxorubicin + cyclophosphamide + vincristine + procarbazine + prednisone |
| BEC | cisplatin + epirubicin + Bleo |
| BEP | Bleo + etoposide + cisplatin |

TABLE 1-continued

| | |
|---|---|
| CAE | cyclophosphamide + doxorubicin + etoposide |
| CDEC | cisplatin + doxorubicin + etoposide + cyclophosphamide |
| CE | carboplatin + etoposide |
| CEC | carboplatin + etoposide + cyclophosphamide |
| CEI | carboplatin + etoposide + ifosfamide |
| CEM-TBI | carboplatin + etoposide + melphalan + total body irradiation |
| ChlVPP/EVA hybrid | chlorambucil + vincristine + procarbazine + etoposide + prednisolone + doxorubicin + vinblastine |
| CHOEP | cyclophosphamide + doxorubicin + vincristine + prednisone + etoposide |
| CIDE | cisplatin + ifosfamide + doxorubicin + etoposide |
| Dexa-BEAM | dexamethasone + BCNU + etoposide + cytarabine + melphalan |
| EP | cisplatin + etoposide |
| EPIC | etoposide + prednisolone + ifosfamide + carboplatin |
| ESHAP | etoposide + methylprednisolone + cytarabine + cisplatin |
| ICE | idarubicin + cytarabine + etoposide |
| IVE | ifosfamide + etoposide + epirubicin |
| MIME | mitoguazone + ifosfamide + methotrexate + etoposide |
| MINE | ifosfamide + mitoxantrone + etoposide |
| POMMB/ACE | vincristine + methotrexate + folinic acid + bleomycin + cisplatin then dactinomycin + cyclophosphamide + etoposide |
| R-ICE | rituximab + ifosfamide + carboplatin + etoposide |
| VIP | ifosfamide + etoposide + cisplatin |
| (V)-ICE | carboplatin + ifosfamide + etoposide + vincristine |
| PACEBOM | prednisolone + doxorubicin + cyclophosphamide + etoposide + bleomycin + vincristine + methotrexate |
| Irinotecan (Campto ®, Camptosar ®) | |
| FOLFIRI | 5-FU + leucovorin + irinotecan |
| Doxorubicin (Doxil ®, Adriamycin ®, Rubix ®) | |
| ABVD | doxorubicin + Bleo + vinblastine + dacarbazine |
| AC | doxorubicin + cyclophosphamide |
| A-CMF | doxorubicin followed by cyclophosphamide + methotrexate + 5-FU |
| AD | doxorubicin + dacarbazine |
| AIM | Doxorubicin + Ifosfamide + Mesna |
| AP | doxorubicin + cisplatin |
| ASHAP | doxorubicin + cisplatin + cytarabine + methylprednisolone |
| A-T-C | doxorubicin followed by paclitaxel followed by cyclophosphamide |
| BEACOPP | bleomycin + etoposide + doxorubicin + cyclophosphamide + vincristine + procarbazine + prednisone |
| CAV | doxorubicin + cyclophosphamide + vincristine |
| CADO | cyclophosphamide + vincristine + doxorubicin |
| CDEC | cisplatin + doxorubicin + etoposide + cyclophosphamide |
| ChlVPP/EVA hybrid | chlorambucil + vincristine + procarbazine + etoposide + prednisolone + doxorubicin + vinblastine |
| CHOP | cyclophosphamide + doxorubicin + vincristine + prednisone |
| CIDE | cisplatin + ifosfamide + doxorubicin + etoposide |
| COPP-ABVD alternating | cyclophosphamide + vincristine + procarbazine + prednisone + doxorubicin + bleomycin + vinblastine + dacarbazine |
| DVD | liposomal doxorubicin + vincristine + dexamethasone |
| ET-2 | ifosfamide + vincristine + doxorubicin + dactinomycin + cyclophosphamide |
| EVAIA | etoposide + vincristine + doxorubicin + ifosfamide + dactinomycin |
| FAC | 5-FU + doxorubicin + cyclophosphamide |
| FAM | 5-FU + doxorubicin + mitomycin |
| FAMTX | methotrexate + 5-FU + leucovorin + doxorubicin |
| MAID | Mesna + Doxorubicin + Ifosfamide + Dacarbazine |
| MOPP/ABV hybrid | Nitrogen mustard + vincristine + procarbazine + prednisone + doxorubicin + bleomycin + vinblastine |
| MVAC | methotrexate + vinblastine + doxorubicin + cisplatin |
| PIAF | cisplatin + doxorubicin + 5-FU + interferon alpha |
| Stanford V | doxorubicin + vinblastine + nitrogen mustard + vincristine + bleomycin + etoposide + prednisone |
| TAG | docetaxel + doxorubicin + cyclophosphamide |
| VACA | vincristine + doxorubicin + cyclophosphamide + dactinomycin |
| VAD | vincristine + doxorubicin + dexamethasone |
| VAIA | vincristine + doxorubicin + ifosfamide + dactinomycin |
| Gemcitabine (Gemzar ®) | |
| GIN | gemcitabine + ifosfamide + vinorelbine |

REFERENCES

1. Rogakou, E. P et al. J Biol Chem 273, 5858-68 (1998).
2. Fernandez-Capetillo, O et al. DNA Repair (Amst) 3, 959-67 (2004).
3. Lowndes, N. F. et al. Curr Biol 15, R99-R102 (2005).
4. Allende-Vega, N. et al. Mol Cell Biochem 274, 85-90 (2005).
5. Cheung, W. L. et al. Curr Biol 15, 656-60 (2005).
6. Loizou, J. I. et al. Cell 117, 17-28 (2004).
7. Festenstein, R. et al. Science 299, 719-21 (2003).
8. Cheutin, T. et al. Science 299, 721-5 (2003).
9. Schmiedeberg, L. et al. Mol Biol Cell 15, 2819-33 (2004).
10. Lukas, C. et al. Nat Cell Biol 5, 255-60 (2003).
11. Rogakou, E. P. et al. J Cell Biol 146, 905-16 (1999).
12. Kruhlak, M. J. et al. J Cell Biol 172, 823-34 (2006).
13. Kuo, M. H. et al. Nature 383, 269-72 (1996).
14. Zhao, T. & Eissenberg, J. C. J Biol Chem 274, 15095-100 (1999).
15. Zhao, T. et al. J Biol Chem 276, 9512-8 (2001).
16. Jacobs, S. A. et al. Science 295, 2080-3 (2002).
17. Formby, B. & Stern, R. Mol Cell Biochem 187, 23-31 (1998).
18. Ruzzene, M. et al Biochem J 364, 41-7 (2002).
19. Canton, D. A et al Biochem J 358, 87-94 (2001).
20. Bakkenist, C. J. et al Nature 421, 499-506 (2003).
21. Ziv, Y. et al et al Nat Cell Biol 8, 870-6 (2006).
22. Jung-Ae Kim, M. K. et al J. Cell Biol 178, 209-218 (2007).
23. Cowell, I. G. et al. PLoS ONE 2, e1057 (2007).
24. Olsten, M. E., et al Mol Cell Biochem 274, 115-24 (2005).
25. Matsuoka, S. et al. Science 316, 1160-6 (2007).
26. Lomberk, G. et al Nat Cell Biol 8, 407-15 (2006).
27. Daniels, M. J. et al. Nat Struct Mol Biol 11, 1114-21 (2004).
28. Rogakou, E. P. et al J Cell Biol 146, 905-16 (1999).
29. Ayoub, N. et al. (2008). Nature 453, 682-686
30. Bonner, W. M. et al (2008) Nat Rev Cancer 8, 957-967.
31. Gorgoulis, V. G. et al. (2005) Nature 434, 907-913.
32. Lobrich, M. et al Proc Natl Acad Sci USA 102, 8984-8989.
33. Sedelnikova, O. A. et al (2006 Cell Cycle 5, 2909-2913.

---

The invention claimed is:

1. A method of assessing DNA damage in a cell comprising:
   determining the presence or amount of Thr51 phosphorylated HP1β protein in the cell,
   wherein the presence or amount of Thr51 phosphorylated HP1β protein is indicative of DNA damage in the cell.

2. The method according to claim 1 wherein the cell is a cultured cell.

3. The method according to claim 1 wherein the cell is in a sample obtained from an individual.

4. The method according to claim 1 wherein the presence or amount of Thr51 phosphorylated HP1β protein is determined by determining the binding of HP1β in the cell to an antibody which specifically binds to Thr51 phosphorylated HP1β protein.

5. The method according to claim 1 wherein the presence or amount of Thr51 phosphorylated HP1β protein is determined in vitro.

* * * * *

UNITED STATES PATENT AND TRADEMARK OFFICE
CERTIFICATE OF CORRECTION

PATENT NO. : 8,021,851 B2  Page 1 of 1
APPLICATION NO. : 12/418038
DATED : September 20, 2011
INVENTOR(S) : Ashok Venkitaraman It is certified that error appears in the above-identified patent and that said Letters Patent is hereby corrected as shown below:

- On the front page of the patent, please add the priority data:

--Related U.S. Application Data

(60) Provisional application No. 61/123,008 filed on April 04, 2008.--

Signed and Sealed this

Eleventh Day of September, 2012

David J. Kappos
*Director of the United States Patent and Trademark Office*

SEQUENCE LISTING

```
<160> NUMBER OF SEQ ID NOS: 1

<210> SEQ ID NO 1
<211> LENGTH: 185
<212> TYPE: PRT
<213> ORGANISM: Homo sapiens

<400> SEQUENCE: 1

Met Gly Lys Lys Gln Asn Lys Lys Val Glu Glu Val Leu Glu Glu
 1               5                   10                  15

Glu Glu Glu Glu Tyr Val Val Glu Lys Val Leu Asp Arg Arg Val Val
                20                  25                  30

Lys Gly Lys Val Glu Tyr Leu Leu Lys Trp Lys Gly Phe Ser Asp Glu
            35                  40                  45

Asp Asn Thr Trp Glu Pro Glu Glu Asn Leu Asp Cys Pro Asp Leu Ile
        50                  55                  60

Ala Glu Phe Leu Gln Ser Gln Lys Thr Ala His Glu Thr Asp Lys Ser
65                  70                  75                  80

Glu Gly Gly Lys Arg Lys Ala Asp Ser Asp Ser Glu Asp Lys Gly Glu
                85                  90                  95

Glu Ser Lys Pro Lys Lys Lys Glu Glu Ser Glu Lys Pro Arg Gly
                100                 105                 110

Phe Ala Arg Gly Leu Glu Pro Glu Arg Ile Ile Gly Ala Thr Asp Ser
            115                 120                 125

Ser Gly Glu Leu Met Phe Leu Met Lys Trp Lys Asn Ser Asp Glu Ala
        130                 135                 140

Asp Leu Val Pro Ala Lys Glu Ala Asn Val Lys Cys Pro Gln Val Val
145                 150                 155                 160

Ile Ser Phe Tyr Glu Glu Arg Leu Thr Trp His Ser Tyr Pro Ser Glu
                165                 170                 175

Asp Asp Asp Lys Lys Asp Asp Lys Asn
                180                 185
```